(12) United States Patent
Wan et al.

(10) Patent No.: US 8,859,797 B1
(45) Date of Patent: Oct. 14, 2014

(54) SYNTHESIS METHODS FOR CARBOSILANES

(71) Applicants: Air Liquide Electronics U.S. LP, Dallas, TX (US); 03;L'Air Liquide, Société Anonyme pour l'Etude et l'Exploitation des Procédés Georges Claude, Paris (FR); American Air Liquide, Inc., Fremont, CA (US)

(72) Inventors: Zhiwen Wan, Plano, TX (US); Ziyun Wang, Allen, TX (US); Ashulosh Misra, Plano, TX (US); Jean-Marc Girard, Versailles (FR); Claudia Fafard, Newark, DE (US); Andrey V. Korolev, Germantown, WI (US)

(73) Assignees: Air Liquide Electronics U.S. LP, Houston, TX (US); L'Air Liquide, Société Anonyme pour l'Etude et l'Exploitation des Procédés Georges Claude, Paris (FR); American Air Liquide, Inc., Fremont, CA (US)

( * ) Notice: Subject to any disclaimer, the term of this patent is extended or adjusted under 35 U.S.C. 154(b) by 0 days.

(21) Appl. No.: 13/973,911

(22) Filed: Aug. 22, 2013

Related U.S. Application Data

(63) Continuation-in-part of application No. 13/458,579, filed on Apr. 27, 2012.

(60) Provisional application No. 61/692,365, filed on Aug. 23, 2012.

(51) Int. Cl.
  *C07F 7/18* (2006.01)
  *C07F 7/08* (2006.01)

(52) U.S. Cl.
  CPC ................................. *C07F 7/0801* (2013.01)
  USPC .......................................... 556/480; 556/478

(58) Field of Classification Search
  CPC ..... C08F 4/6578; C08F 4/6355; C07F 7/1868
  USPC .......................................... 556/400, 478, 480
  See application file for complete search history.

(56) References Cited

U.S. PATENT DOCUMENTS

| | | | |
|---|---|---|---|
| 5,153,295 A * | 10/1992 | Whitmarsh et al. | 528/31 |
| 6,521,774 B2 * | 2/2003 | Koike et al. | 556/435 |
| 6,730,802 B2 * | 5/2004 | Shen et al. | 556/12 |
| 6,800,133 B1 | 10/2004 | Kim et al. | |
| 2002/0002299 A1 * | 1/2002 | Arkles et al. | 556/478 |
| 2013/0274497 A1 | 10/2013 | Larson et al. | |

FOREIGN PATENT DOCUMENTS

WO  WO 95 10638  4/1995

OTHER PUBLICATIONS

Bazant et al; Collection czechoslov. Chemical Communication, 1974, vol. 39, 1735-1739.*

Jung et al., "Si—C coupling reaction of polychloromethanes with $HSiCl_3$ in the presence of $Bu_4PCl$: Convenient synthetic method for bis(chlorosilyl)methanes," Journal of Organometallic Chemistry (2007) 692(18) 3901-3906.

Shimizu et al., "1,1,3,3-tetrakis(alkylthio)-1,3-dilithio-2-silapropanes: useful reagents for the synthesis of polysilacycloalkanes via dianionic ring formation," Arkivoc (2007) 29-48.

Birot, M. et al., "Comprehensive chemistry of polycarbosilanes, polysilazanes, and polycarbosilazanes as precursors of ceramics," Chem. Rev. 1995, 95, pp. 1443-1477.

Bobrovsky, A.Y. et al., "Photochemical and photoorientational behavior of liquid crystaliine carbosilane dendrimer with azobenzene terminal groups," J. Phys. Chem. B 2002, 106, pp. 540-546.

Boo, J.-H. et al., "Epitaxial growth of cubic SiC thin films on silicon using single molecular precursors by metalorganic chemical vapor deposition," J. Vac. Sci. Technol. A 19(4), Jul./Aug. 2001, pp. 1887-1893.

Brefort, J.L. et al., "New poly[(silylene)diacetylenes] and poly[(germylene) diacetylenes]: Synthesis and conductive properties," Organometallics 1992, 11, pp. 2500-2506.

Brondani, D.J. et al., " A new triaikoxysilylation reaction, the cross-coupling of (tri-isopropyloxysilyl) methyl grignard reagent: with organic halides," J. Org. Chem., 1993, vol. 451, pp. C1-C3.

Brondani, D.J. et al., "Polyfunctional carbosilanes and organosilicon compounds. syntheses via Grignard reactions," Tetrahedron Letters, 34, 13, 1993, pp. 2111-2114.

Corriu, R.J.P. et al., "One-step route to silicon carbide precursors by a tunable catalytic polycondensation," Chem. Mater. 1994, 6, pp. 15-17.

Daiss, J.O. et al., "Synthesis of the multifunctional (chloromethyl)silanes $Cl_2Si(CH_2Cl)_2$, $(MeO)_2Si(CH_2Cl)_2$, $RSi(SCH_2Cl)_3$ $_{(R=2,4,6\text{-}trimethoxyphenyl)}$, $ClSi(CH_2Cl)_3$, $MeOSi(CH_2Cl)_3$, $Si(CH_2Cl)_4$, and $ClCH_2CH_2Si(CH_2Cl)_3$,§" Organometallics 2004, 23, p. 5193-5197.

Dannels, B.F. et al., "Studies in organosilicon chemistry. XXXIV. The reaction of trimethylsilylmethyl metallic compounds with trichlorosilane," vol. 22, 1956, pp. 748-750.

Gevorgyan, V. et al., "Silatranes from reactions of chloromethylsilatrane with chlorosilanes and magnesium in tetrahydrofuran," J. Org. Chem., 1991, vol. 418, pp. C21-C23.

Han, W.-S. et al., "Silane-based hydrogen storage materials for fuel cell application: Hydrogen release via methanolysis and regeneration by hydride reduction from organosilanes," Int'l Journal of Hydrogen Energy 36, 2001, pp. 12305-12312.

Handmann, V.I. et al., "New bicyclic sila-heterocycles: Syntheses and crystal structure analyses of rac -7-ethoxy-2,2-diorganyl-2,3,4,5a-tetrahydro-1H-3a,6-diaza-2-sila-inden-4-ones," Journal of Organometallic Chemistry 613, 2000, pp. 19-25.

(Continued)

Primary Examiner — Sudhakar Katakam
Assistant Examiner — Pancham Bakshi
(74) Attorney, Agent, or Firm — Patricia E. McQueeney

(57) ABSTRACT

A $SiH[CH_2—Si(OEt)_3]_3$ carbosilane compound is synthesized by reacting a Grignard reagent having the formula $Si(OEt)_3(CH_2MgCl)$ with a quenching agent having the formula $SiHCl_3$.

5 Claims, 5 Drawing Sheets

(56) References Cited

OTHER PUBLICATIONS

Hong, S.H. et al., "Phosohine-catalyzed Si—C coupling of bis-silylmethanes: Preparation of cyclic $(Cl_2SiCH_2)_2$ and linear $Cl_2Si(CH_2SiCl_3)_2$ via silylene and silene intermediates,"Organometallics 2010, 29, pp. 687-691.

Jung, I.N. et al., "Direct synthesis of trisilaalkanes," Bull. Korean Chem. Soc., 12, 4, 1961, pp. 445-449

Kang, S.-H. et al., "Phosphonium chloride-catalyzed dehydrochlorinative coupling reactions of alkyl halides with hydridochlorosilanes," Organometallics 2003, 22, pp. 529-534.

Laine, R.M., "Preceramic polymer routes to silicon carbide," Chem. Mater. 1993, 5, pp. 260-279.

Lee, T. et al., "Highly efficient hydrosilylation of diyne and triyne π-electron bridges: Its application to fluorescent dyes and silylene-spaced vinylarene compounds," Organometallics 2004, 23, pp. 4184-4191

Li, C.-F. et al., "Photoluminescense of PMMA doped with fluorescein and carbosilane dendrimer and lasiing PBG resonance cavity," Journal of Luminescense 127, 2007, pp. 321-326.

Mirskov, R.G. et al., "High-purity alkoxychlorosilanes as precursors for precipitation of silica," Doklady Chemistry, 2008, vol. 421, Part 2, pp. 194-196.

Ohshita, J. et al., "Polymeric organosilicon systems. 11. Synthesis and some properties of poly(disilanylenebutenyne-1,4-diyls) and poly[(methylphenylsilylen)butenyne-1,4-diyl][1]," Macromolecules 1992, 25, pp. 2134-2140.

Seyferth, D., "Polycarbosilanes: an overview," Inorganic and Organometallic Polymers, Chapter 3, ACS Symposium Series 360, ACS: Washington, DC, 1988, pp. 21-42.

Son, H.-J. et al., "Electrochemical deposition of end-capped triarylamine and carbazole.dendrimers: Alternate technique for the manufacture of multilayer films," Chem. Mater. 18, 25, Dec. 12, 2006, pp. 5811-5813.

Speier, J.L. et al., "Relative consecutive competitive rates of alkoxylation of chlorosilanes," Organometallics 1993, 12, pp. 1981-1982.

Whitmarsh, C.K. et al., "Synthesis and structure of a highly branched polycarbosilane derived from (chloromethyl)trichlorosilane," Organometallics 1991, 10, pp. 1336-1344.

Yoo, B.R. et al., "Synthesis of organosilicon compounds by new direct reactions," Advances in Organometallic Chemistry, 2005, vol. 50, pp. 145-177.

Hassler, K. et al., "The (chloromethyl)dihalosilanes $X_2HSiCH_2Cl$ (X= F, Cl, Br, I): synthesis, multinuclear NMR spectroscopy and rotational isomerism examined by Raman spectroscopy," Eur. J. lnorg. Chem. 2004, pp. 4259-4265.

Seyferth, D. et al., "The preparation of chloromethyl derivatives of germanium and silicon by the diazomethane method," Journal of American Chemical Society, 1955, 77(4), pp. 907-908.

* cited by examiner

SYNTHESIS METHODS FOR CARBOSILANES

CROSS-REFERENCE TO RELATED APPLICATIONS

This application claims priority to U.S. application No. 61/692,365, filed Aug. 23, 2012, the entire contents of which are incorporated herein by reference. This application is also a continuation-in-part of prior application Ser. No. 13/458,579, filed Apr. 27, 2012, the entire contents of which are incorporated herein by reference.

TECHNICAL FIELD

Disclosed are synthesis methods to produce carbosilanes.

BACKGROUND

Carbosilanes, i.e. linear or branched molecules with a backbone having alternate Si and C atoms and at least one Si—C—Si unit, are attracting attention owing to their chemical properties and potential usage in various fields such as ceramics, optical coatings, electronics, semiconductors, and hydrogen storage. However, the synthesis of such compounds has proven to be relatively difficult, partially due to the fact that a mixture of compounds may be produced. In addition the low yield of such methods increases the cost of making the targeted compound.

Controlled Si—C—Si unit synthesis has been achieved using a Grignard method. Gevorgyan et al. (J. Org. Chem. 418, 1991 C21-C23) disclose the formation of $R_3Si$—$CH_2$—$Si(OCH_2CH_2)_3N$ from $ClCH_2$—$Si(OCH_2CH_2)_3N$ and $R_3Si$—Cl in the presence of magnesium in THF, with $R_3$ being $Me_3$, $Me_2Ph$, $MePh_2$, $HMe_2$, or $HMePh$. Brondani et al. (J. Org. Chem. 451, 1993 C1-C3) disclose cross-coupling of (tri-isopropyloxysilyl) methyl Grignard reagents with organic halides to form trialkoxysilylated organic compounds. U.S. Pat. No. 5,153,295 to Whitmarsh et al. discloses that the diethylamino group of a $CISKNEt_2)_2CH_2ClGrignard$ reagent blocks two chlorine sites preventing branching of the carbosilane polymer. U.S. Pat. No. 6,730,802 to Shen et al. discloses synthesis of 2,4,6-trimethyl-2,4,6-trisilaheptane by reducing chloromethyl-dimethylchlorosilane with lithium aluminum hydride, reacting the resulting chloromethyldimethylsilane with magnesium to form the corresponding Grignard reagent, and coupling the Grignard reagent with methyldichlorosilane.

For some specific applications, obtaining a pure product is critical for the stability of the process that uses the product, and such non-discriminating synthesis methods are costly since they involve expensive separation processes to obtain the target compound. A need remains for a cost effective synthesis method of linear or branched carbosilanes.

NOTATION AND NOMENCLATURE

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "carbosilane" refers to a linear or branched molecule with a backbone having alternate Si and C atoms and at least one Si—C—Si unit; the term "Grignard reagent" refers to organomagnesium halides having the formula $Si(OR')_xH_yR_z(CH_2MgX)$, wherein x=0 to 3; y=0 to 1; z=0 to 3; x+y+z=3; X=Cl, Br, or I; each R is independently a C1 to C5 linear or branched alkyl group or a trimethylsilyl group; and each R' is independently a C1 to C5 linear or branched alkyl group, even though the claimed Grignard reagents are not used in a Grignard reaction; the term "quenching" refers to the reaction of the Grignard reagent with the quenching agent; the term "quenching agent" refers to the compound that "deactivates" the Grignard reagent by reacting with the Grignard reagent to produce a Mg salt compound.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the term "aryl" refers to aromatic ring compounds where one hydrogen atom has been removed from the ring. As used herein, the term "heterocycle" refers to a cyclic compound that has atoms of at least two different elements as members of its ring.

As used herein, the abbreviation "Me" refers to a methyl group; the abbreviation "Et" refers to an ethyl group; the abbreviation "Pr" refers to any propyl group (i.e., n-propyl or isopropyl); the abbreviation "iPr" refers to an isopropyl group; the abbreviation "Bu" refers to any butyl group (n-butyl, iso-butyl, t-butyl, sec-butyl); the abbreviation "tBu" refers to a tert-butyl group; the abbreviation "sBu" refers to a sec-butyl group; the abbreviation "iBu" refers to an iso-butyl group; the abbreviation "ph" refers to a phenyl group; the abbreviation "Am" refers to any amyl group (iso-amyl, sec-amyl, tert-amyl); the abbreviation "Cy" refers to a cyclic alkyl group (cyclobutyl, cyclopentyl, cyclohexyl, etc.); and the abbreviation GCMS stands for Gas Chromatography/Mass Spectrometry.

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.).

SUMMARY

Disclosed are methods of synthesizing a carbosilane compound by reacting a Grignard reagent having the formula $Si(OR')_xH_yR_z(CH_2MgX)$ with a quenching agent having the formula $SiCl_a(OR)_b(H)_c$ to produce $Si(OR)_b(H)_c[CH_2-Si(OR')_xH_yR_z]_a$, wherein a=1 to 3; b=0 to 3; c=0 to 2; a+b+c=4; x=0 to 3; y=0 to 1; z=0 to 3; x+y+z=3; X=Cl, Br, or I; each R is independently a C1 to C5 linear or branched alkyl group or a trimethylsilyl group; and each R' is independently a C1 to C5 linear or branched alkyl group. The disclosed methods may further include one or more of the following aspects:

- a molar ratio of the Grignard reagent $Si(OR')_xH_yR_z(CH_2MgX)$ to the quenching agent $SiCl_a(OR)_b(H)_c$ is between approximately 0.8 and approximately 4.5;
- forming the Grignard reagent $Si(OR')_xH_yR_z(CH_2MgX)$ in-situ by reacting $Si(OR')_xH_yR_z(CH_2X)$ over magnesium;
- maintaining a temperature of formation of the Grignard reagent between approximately 0° C. to approximately 20° C.
- the step of forming the Grignard reagent $Si(OR')_xH_yR_z(CH_2MgX)$ occurring in a same vessel as the step of reacting the Grignard reagent and the quenching agent;
- reducing $Si(OR)_b(H)_c[CH_2—Si(OR')_xH_yR_z]_a$ by $AlLiH_4$ in ether to form a compound having a formula $SiH_{b+c}[CH_2—SiH_{x+y}Rz]_{4-b-c}$, wherein b=0 to 3; c=0 to 2; b+c=1 to 3; x=0 to 3; y=0 to 1; z=0 to 3; x+y+z=3; and each R is independently a C1 to C5 linear or branched alkyl group or a trimethylsilyl group;
- a molar ratio of $AlLiH_4$ to $Si(OR)_b(H)_c[CH_2—Si(OR')_xH_yR_z]_a$ being between approximately (b+ax)/4 and approximately (b+ax)/2, wherein b=0 to 3, a=1 to 3, and x=0 to 3;
- reducing $Si(OR)_b(H)_c[CH_2—Si(OR')_xH_yR_z]_a$ by $NaBH_4$ in ether to form $SiH_{b+c}[CH_2—SiH_{x+y}R_z]_{4-b-c}$, wherein b=0 to 3; c=0 to 2; b+c=1 to 3; x=0 to 3; y=0 to 1; z=0 to 3; x+y+z=3; and each R is independently a C1 to C5 linear or branched alkyl group or a trimethylsilyl group;
- a molar ratio of $NaBH_4$ to $Si(OR)_b(H)_c[CH_2—Si(OR')_xH_yR_z]_a$ being between approximately (b+ax)/4 and approximately (b+ax)/2, wherein b=0 to 3, a=1 to 3, and x=0 to 3;
- x=3, y=0, z=0, and R'=Me or Et;
- the Grignard reagent being $Si(OR')_3(CH_2MgCl)$;
- a=3, b=0, and c=1;
- the quenching agent being $SiHCl_3$;

Also disclosed are methods of synthesizing a carbosilane compound by in situ quenching of a Grignard reagent having the formula $Si(OR')_xH_yR_z(CH_2MgX)$ with a quenching agent having the formula $SiCl_a(OR)_b(H)_c$ to produce $Si(OR)_b(H)_c[CH_2—Si(OR')_xH_yR_z]_a$, wherein a=1 to 3; b=0 to 3; c=0 to 2; a+b+c=4; x=0 to 3; y=0 to 1; z=0 to 3; x+y+z=3; X=Cl, Br, or I; each R is independently a C1 to C5 linear or branched alkyl group or a trimethylsilyl group; and each R' is independently a C1 to C5 linear or branched alkyl group.

Also disclosed are methods of synthesizing a carbolsilane compound by reacting a Grignard reagent having the formula $Si(OEt)_3(CH_2MgCl)$ with a quenching agent having the formula $SiHCl_3$ to produce $SiH[CH_2—Si(OEt)_3]_3$. The disclosed methods may further include one or more of the following aspects:

- forming the Grignard reagent $Si(OEt)_3(CH_2MgCl)$ by reacting $Si(OEt)_3(CH_2Cl)$ over magnesium;
- maintaining a temperature of formation of the Grignard reagent between approximately 0° C. to approximately 20° C.
- the step of forming the Grignard reagent $Si(OEt)_3(CH_2MgCl)$ occurring in a same vessel as the step of reacting the Grignard reagent and the quenching agent; and
- reducing $SiH[CH_2—Si(OEt)_3]_3$ to form a compound having a formula $SiH[CH_2—SiH_3]_3$.

BRIEF DESCRIPTION OF THE FIGURES

For a further understanding of the nature and objects of the present invention, reference should be made to the following detailed description, taken in conjunction with the accompanying figures wherein.

DESCRIPTION OF PREFERRED EMBODIMENTS

Figure 1:
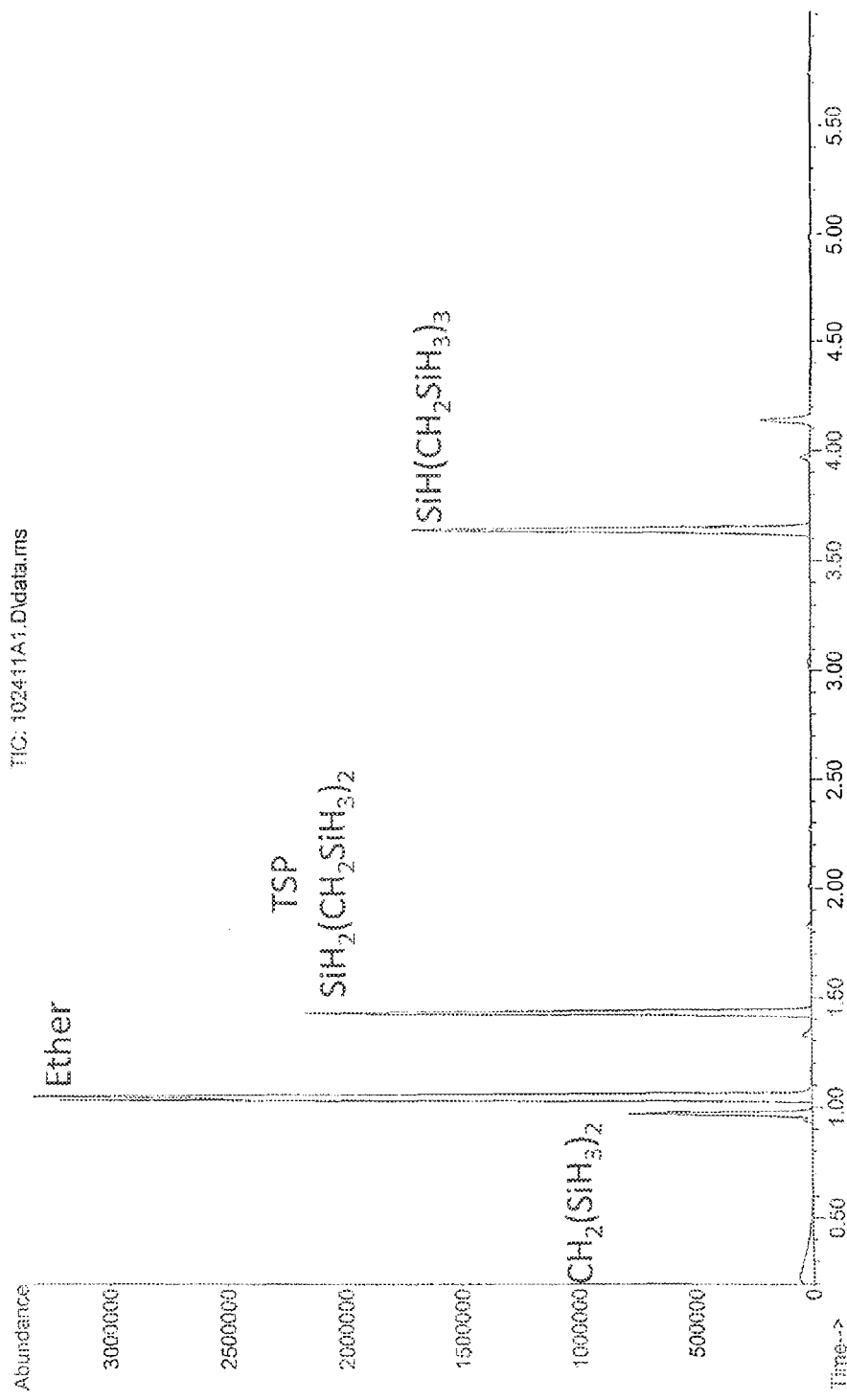
FIG. 1 is a gas chromatograph/mass spectrometer (GCMS) graph of the product synthesized in the Comparative Example.

Disclosed are methods of synthesizing compounds having the formula $Si(OR)_b(H)_c[CH_2—Si(OR')_xH_yR_z]_a$, wherein a=1 to 3; b=0 to 3; c=0 to 2; a+b+c=4; x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group. These compounds may be used in the field of ceramics, optical coatings, electronics (i.e., devices), semiconductors (i.e., components), hydrogen storage, and semiconductor components that may be used at least in electronic devices.

In some embodiments, x=3, y=0, z=0, and R'=Me or Et to produce $Si(OR)_b(H)_c[CH_2—Si(OMe)_3]_a$ and $Si(OR)_b(H)_c[CH_2—Si(OEt)_3]_a$, wherein a=1 to 3; b=0 to 3; c=0 to 2; a+b+c=4; and each R is independently a C1 to C5 linear or branched alkyl group or a trimethylsilyl ($SiMe_3$) group.

Exemplary compounds wherein x=3, y=0, z=0, R'=Me or Et, a=3, b=0, and c=1 include $SiH[CH_2—Si(OMe)_3]_3$ and $SiH[CH_2—Si(OEt)_3]_3$.

Exemplary compounds wherein x=3, y=0, z=0, R'=Me or Et, a=3, b=1, and c=0 include $Si(OMe)[CH_2—Si(OMe)_3]_3$, $Si(OMe)[CH_2—Si(OEt)_3]_3$, $Si(OEt)[CH_2—Si(OMe)_3]_3$, $Si(OEt)[CH_2—Si(OEt)_3]_3$, $Si(OiPr)[CH_2—Si(OMe)_3]_3$, $Si(OiPr)[CH_2—Si(OEt)_3]_3$, $Si(OnPr)[CH_2—Si(OMe)_3]_3$, $Si(OnPr)[CH_2—Si(OEt)_3]_3$, $Si(OnBu)[CH_2—Si(OMe)_3]_3$, $Si(OnBu)[CH_2—Si(OEt)_3]_3$, $Si(OtBu)[CH_2—Si(OMe)_3]_3$, $Si(OtBu)[CH_2—Si(OEt)_3]_3$, $SKOiBu)[CH_2—Si(OMe)_3]_3$, $Si(OiBu)[CH_2—Si(OEt)_3]_3$, $Si(OSiMe_3)[CH_2—Si(OMe)_3]_3$, and $Si(OSiMe_3)[CH_2—Si(OD)_3]_3$.

Exemplary compounds wherein x=3, y=0, z=0, R'=Me or Et, a=2, b=0, and c=2 include $SiH_2[CH_2—Si(OMe)_3]_2$ and $SiH_2[CH_2—Si(OEt)_3]_2$.

Exemplary compounds wherein x=3, y=0, z=0, R'=Me or Et, a=2, b=2, and c=0 include $Si(OMe)_2[CH_2—Si(OMe)_3]_2$, $Si(OMe)_2[CH_2—Si(OEt)_3]_2$, $Si(OEt)_2[CH_2—Si(OMe)_3]_2$, $Si(OEt)_2[CH_2—Si(OEt)_3]_2$, $Si(OiPr)_2[CH_2—Si(OMe)_3]_2$, $Si(OiPr)_2[CH_2—Si(OEt)_3]_2$, $Si(OnPr)_2[CH_2—Si(OMe)_3]_2$, $Si(OnPr)_2[CH_2—Si(OEt)_3]_2$, $Si(OnBu)_2[CH_2—Si(OMe)_3]_2$, $Si(OnBu)_2[CH_2—Si(OEt)_3]_2$, $Si(OtBu)_2[CH_2—Si(OMe)_3]_2$, $Si(OtBu)_2[CH_2—Si(OEt)_3]_2$, $Si(OiBu)_2[CH_2—Si(OMe)_3]_2$, $Si(OiBu)_2[CH_2—Si(OEt)_3]_2$, $Si(OSiMe_3)_2[CH_2—Si(OMe)_3]_2$ and $Si(OSiMe_3)_2[CH_2—Si(OEt)_3]_2$.

Exemplary compounds wherein x=3, y=0, z=0, R'=Me or Et, a=2, b=1, and c=1 include $SiH(OMe)[CH_2—Si(OMe)_3]_2$, $SiH(OMe)[CH_2—Si(OEt)_3]_2$, $SiH(OEt)[CH_2—Si(OMe)_3]_2$, $SiH(OEt)[CH_2—Si(OEt)_3]_2$, $SiH(OiPr)[CH_2—Si(OMe)_3]_2$, $SiH(OiPr)[CH_2—Si(OEt)_3]_2$, $SiH(OnPr)[CH_2—Si(OMe)_3]_2$, $SiH(OnPr)[CH_2—Si(OEt)_3]_2$, $SiH(OnBu)[CH_2—Si(OMe)_3]_2$, $SiH(OnBu)[CH_2—Si(OEt)_3]_2$, $SiH(OtBu)[CH_2—Si(OMe)_3]_2$, $SiH(OtBu)[CH_2—Si(OEt)_3]_2$, SiH(OiBu)[CH$_2$—Si(OMe)$_3$]$_2$, SiH(OiBu)[CH$_2$—Si(OEt)$_3$]$_2$, SiH(OSiMe$_3$)[CH$_2$—Si(OMe)$_3$]$_2$, and SiH(OSiMe$_3$)[CH$_2$—Si(OEt)$_3$]$_2$.

Exemplary compounds wherein x=3, y=0, z=0, R'=Me or Et, a=1, b=1, and c=2 include SiH$_2$(OMe)[CH$_2$—Si(OMe)$_3$], SiH$_2$(OMe)[CH$_2$—Si(OEt)$_3$], SiH$_2$(OEt)[CH$_2$—Si(OMe)$_3$], SiH$_2$(OEt)[CH$_2$—Si(OEt)$_3$], SiH$_2$(OiPr)[CH$_2$—Si(OMe)$_3$], SiH$_2$(OnPr)[CH$_2$—Si(OEt)$_3$], SiH$_2$(OnPr)[CH$_2$—Si(OMe)$_3$], SiH$_2$(OnPr)[CH$_2$—Si(OEt)$_3$], SiH$_2$(OnBu)[CH$_2$—Si(OMe)$_3$], SiH$_2$(OnBu)[CH$_2$—Si(OEt)$_3$], SiH$_2$(OtBu)[CH$_2$—Si(OMe)$_3$], SiH$_2$(OtBu)[CH$_2$—Si(OEt)$_3$], SiH$_2$(OiBu)[CH$_2$—Si(OMe)$_3$], SiH$_2$(OiBu)[CH$_2$—Si(OEt)$_3$], SiH$_2$(OSiMe$_3$)[CH$_2$—Si(OMe)$_3$], and SiH$_2$(OSiMe$_3$)[CH$_2$—Si(OEt)$_3$].

Exemplary compounds wherein x=3, y=0, z=0, R'=Me or Et, a=1, b=2, and c=1 include SiH(OMe)$_2$[CH$_2$—Si(OMe)$_3$], SiH(OMe)$_2$[CH$_2$—Si(OEt)$_3$], SiH(OEt)$_2$[CH$_2$—Si(OMe)$_3$], SiH(OEt)$_2$[CH$_2$—Si(OEt)$_3$], SiH(OiPr)$_2$[CH$_2$—Si(OMe)$_3$], SiH(OiPr)$_2$[CH$_2$—Si(OEt)$_3$], SiH(OnPr)$_2$[CH$_2$—Si(OMe)$_3$], SiH(OnPr)$_2$[CH$_2$—Si(OEt)$_3$], SiH(OnBu)$_2$[CH$_2$—Si(OMe)$_3$], SiH(OnBu)$_2$[CH$_2$—Si(OEt)$_3$], SiH(OtBu)$_2$[CH$_2$—Si(OMe)$_3$], SiH(OtBu)$_2$[CH$_2$—Si(OEt)$_3$], SiH(OiBu)$_2$[CH$_2$—Si(OMe)$_3$], SiH(OiBu)$_2$[CH$_2$—Si(OEt)$_3$], SiH(OSiMe$_3$)$_2$[CH$_2$—Si(OMe)$_3$], and SiH(OSiMe$_3$)$_2$[CH$_2$—Si(OEt)$_3$].

Exemplary compounds wherein x=3, y=0, z=0, R'=Me or Et, a=1, b=3, and c=0 include Si(OMe)$_3$[CH$_2$—Si(OMe)$_3$], Si(OMe)$_3$[CH$_2$—Si(OEt)$_3$], Si(OEt)$_3$[CH$_2$—Si(OMe)$_3$], Si(OEt)$_3$[CH$_2$—Si(OEt)$_3$], Si(OiPr)$_3$[CH$_2$—Si(OMe)$_3$], Si(OiPr)$_3$[CH$_2$—Si(OEt)$_3$], Si(OnPr)$_3$[CH$_2$—Si(OMe)$_3$], Si(OnPr)$_3$[CH$_2$—Si(OEt)$_3$], Si(OnBu)$_3$[CH$_2$—Si(OMe)$_3$], Si(OnBu)$_3$[CH$_2$—Si(OEt)$_3$], Si(OtBu)$_3$[CH$_2$—Si(OMe)$_3$], Si(OtBu)$_3$[CH$_2$—Si(OEt)$_3$], Si(OiBu)$_3$[CH$_2$—Si(OMe)$_3$], Si(OiBu)$_3$[CH$_2$—Si(OEt)$_3$], Si(OSiMe$_3$)$_3$[CH$_2$—Si(OMe)$_3$], and Si(OSiMe$_3$)$_3$[CH$_2$—Si(OEt)$_3$].

In some embodiments, a=2, b=2, and c=0 to produce Si(OR)$_2$[CH$_2$—Si(OR')$_x$H$_y$R$_z$]$_2$, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group.

Exemplary compounds wherein a=2, b=2, c=0, x=3, y=0, and z=0 include Si(OMe)$_2$[CH$_2$—Si(OMe)$_3$]$_2$, Si(OMe)$_2$[CH$_2$—Si(OEt)$_3$]$_2$, Si(OMe)$_2$[CH$_2$—Si(OiPr)$_3$]$_2$, Si(OMe)$_2$[CH$_2$—Si(OnPr)$_3$]$_2$, Si(OMe)$_2$[CH$_2$—Si(OnBu)$_3$]$_2$, Si(OMe)$_2$[CH$_2$—Si(OtBu)$_3$]$_2$, Si(OMe)$_2$[CH$_2$—Si(OiBu)$_3$]$_2$, Si(OEt)$_2$[CH$_2$—Si(OMe)$_3$]$_2$, Si(OEt)$_2$[CH$_2$—Si(OEt)$_3$]$_2$, Si(OEt)$_2$[CH$_2$—Si(OiPr)$_3$]$_2$, Si(OEt)$_2$[CH$_2$—Si(OnPr)$_3$]$_2$, Si(OEt)$_2$[CH$_2$—Si(OnBu)$_3$]$_2$, Si(OEt)$_2$[CH$_2$—Si(OtBu)$_3$]$_2$, Si(OEt)$_2$[CH$_2$—Si(OiBu)$_3$]$_2$, Si(OiPr)$_2$[CH$_2$—Si(OMe)$_3$]$_2$, Si(OiPr)$_2$[CH$_2$—Si(OEt)$_3$]$_2$, Si(OiPr)$_2$[CH$_2$—Si(OiPr)$_3$]$_2$, Si(OiPr)$_2$[CH$_2$—Si(OnPr)$_3$]$_2$, Si(OiPr)$_2$[CH$_2$—Si(OnBu)$_3$]$_2$, Si(OiPr)$_2$[CH$_2$—Si(OtBu)$_3$]$_2$, Si(OiPr)$_2$[CH$_2$—Si(OiBu)$_3$]$_2$, Si(OnPr)$_2$[CH$_2$—Si(OMe)$_3$]$_2$, Si(OnPr)$_2$[CH$_2$—Si(OEt)$_3$]$_2$, Si(OnPr)$_2$[CH$_2$—Si(OiPr)$_3$]$_2$, Si(OnPr)$_2$[CH$_2$—Si(OnPr)$_3$]$_2$, Si(OnPr)$_2$[CH$_2$—Si(OnBu)$_3$]$_2$, Si(OnPr)$_2$[CH$_2$—Si(OtBu)$_3$]$_2$, Si(OnPr)$_2$[CH$_2$—Si(OiBu)$_3$]$_2$, Si(OnBu)$_2$[CH$_2$—Si(OMe)$_3$]$_2$, Si(OnBu)$_2$[CH$_2$—Si(OEt)$_3$]$_2$, Si(OnBu)$_2$[CH$_2$—Si(OiPr)$_3$]$_2$, Si(OnBu)$_2$[CH$_2$—Si(OnPr)$_3$]$_2$, Si(OnBu)$_2$[CH$_2$—Si(OnBu)$_3$]$_2$, Si(OnBu)$_2$[CH$_2$—Si(OtBu)$_3$]$_2$, Si(OnBu)$_2$[CH$_2$—Si(OiBu)$_3$]$_2$, Si(OtBu)$_2$[CH$_2$—Si(OMe)$_3$]$_2$, Si(OtBu)$_2$[CH$_2$—Si(OEt)$_3$]$_2$, Si(OtBu)$_2$[CH$_2$—Si(OiPr)$_3$]$_2$, Si(OtBu)$_2$[CH$_2$—Si(OnPr)$_3$]$_2$, Si(OtBu)$_2$[CH$_2$—Si(OnBu)$_3$]$_2$, Si(OtBu)$_2$[CH$_2$—Si(OtBu)$_3$]$_2$, Si(OtBu)$_2$[CH$_2$—Si(OiBu)$_3$]$_2$, Si(OiBu)$_2$[CH$_2$—Si(OMe)$_3$]$_2$, Si(OiBu)$_2$[CH$_2$—Si(OEt)$_3$]$_2$, Si(OiBu)$_2$[CH$_2$—Si(OiPr)$_3$]$_2$, Si(OiBu)$_2$[CH$_2$—Si(OnPr)$_3$]$_2$, Si(OiBu)$_2$[CH$_2$—Si(OnBu)$_3$]$_2$, Si(OiBu)$_2$[CH$_2$—Si(OtBu)$_3$]$_2$, Si(OiBu)$_2$[CH$_2$—Si(OiBu)$_3$]$_2$, Si(OSiMe$_3$)$_2$[CH$_2$—Si(OMe)$_3$]$_2$, Si(OSiMe$_3$)$_2$[CH$_2$—Si(OEt)$_3$]$_2$, Si(OSiMe$_3$)$_2$[CH$_2$—Si(OiPr)$_3$]$_2$, Si(OSiMe$_3$)$_2$[CH$_2$—Si(OnPr)$_3$]$_2$, Si(OSiMe$_3$)$_2$[CH$_2$—Si(OnBu)$_3$]$_2$, Si(OSiMe$_3$)$_2$[CH$_2$—Si(OiBu)$_3$]$_2$, and Si(OSiMe$_3$)$_2$[CH$_2$—Si(OtBu)$_3$]$_2$.

Exemplary compounds wherein a=2, b=2, c=0, x=2, y=1, and z=0 include Si(OMe)$_2$[CH$_2$—SiH(OMe)$_2$]$_2$, Si(OMe)$_2$[CH$_2$—SiH(OEt)$_2$]$_2$, Si(OMe)$_2$[CH$_2$—SiH(OiPr)$_2$]$_2$, Si(OMe)$_2$[CH$_2$—SiH(OnPr)$_2$]$_2$, Si(OMe)$_2$[CH$_2$—SiH(OnBu)$_2$]$_2$, Si(OMe)$_2$[CH$_2$—SiH(OtBu)$_2$]$_2$, Si(OMe)$_2$[CH$_2$—SiH(OiBu)$_2$]$_2$, Si(OEt)$_2$[CH$_2$—SiH(OMe)$_2$]$_2$, Si(OEt)$_2$[CH$_2$—SiH(OEt)$_2$]$_2$, Si(OEt)$_2$[CH$_2$—SiH(OiPr)$_2$]$_2$, Si(OEt)$_2$[CH$_2$—SiH(OnPr)$_2$]$_2$, Si(OEt)$_2$[CH$_2$—SiH(OnBu)$_2$]$_2$, Si(OEt)$_2$[CH$_2$—SiH(OtBu)$_2$]$_2$, Si(OEt)$_2$[CH$_2$—SiH(OiBu)$_2$]$_2$, Si(OiPr)$_2$[CH$_2$—SiH(OMe)$_2$]$_2$, Si(OiPr)$_2$[CH$_2$—SiH(OEt)$_2$]$_2$, Si(OiPr)$_2$[CH$_2$—SiH(OiPr)$_2$]$_2$, Si(OiPr)$_2$[CH$_2$—SiH(OnPr)$_2$]$_2$, Si(OiPr)$_2$[CH$_2$—SiH(OnBu)$_2$]$_2$, Si(OiPr)$_2$[CH$_2$—SiH(OtBu)$_2$]$_2$, Si(OiPr)$_2$[CH$_2$—SiH(OiBu)$_2$]$_2$, Si(OnPr)$_2$[CH$_2$—SiH(OMe)$_2$]$_2$, Si(OnPr)$_2$[CH$_2$—SiH(OEt)$_2$]$_2$, Si(OnPr)$_2$[CH$_2$—SiH(OiPr)$_2$]$_2$, Si(OnPr)$_2$[CH$_2$—SiH(OnPr)$_2$]$_2$, Si(OnPr)$_2$[CH$_2$—SiH(OnBu)$_2$]$_2$, Si(OnPr)$_2$[CH$_2$—SiH(OtBu)$_2$]$_2$, Si(OnPr)$_2$[CH$_2$—SiH(OiBu)$_2$]$_2$, Si(OnBu)$_2$[CH$_2$—SiH(OMe)$_2$]$_2$, Si(OnBu)$_2$[CH$_2$—SiH(OEt)$_2$]$_2$, Si(OnBu)$_2$[CH$_2$—SiH(OiPr)$_2$]$_2$, Si(OnBu)$_2$[CH$_2$—SiH(OnPr)$_2$]$_2$, Si(OnBu)$_2$[CH$_2$—SiH(OnBu)$_2$]$_2$, Si(OnBu)$_2$[CH$_2$—SiH(OiBu)$_2$]$_2$, Si(OnBu)$_2$[CH$_2$—SiH(OtBu)$_2$]$_2$, Si(OtBu)$_2$[CH$_2$—SiH(OMe)$_2$]$_2$, Si(OtBu)$_2$[CH$_2$—SiH(OEt)$_2$]$_2$, Si(OtBu)$_2$[CH$_2$—SiH(OiPr)$_2$]$_2$, Si(OtBu)$_2$[CH$_2$—SiH(OnPr)$_2$]$_2$, Si(OtBu)$_2$[CH$_2$—SiH(OnBu)$_2$]$_2$, Si(OtBu)$_2$[CH$_2$—SiH(OtBu)$_2$]$_2$, Si(OtBu)$_2$[CH$_2$—SiH(OiBu)$_2$]$_2$, Si(OiBu)$_2$[CH$_2$—SiH(OMe)$_2$]$_2$, Si(OiBu)$_2$[CH$_2$—SiH(OEt)$_2$]$_2$, Si(OiBu)$_2$[CH$_2$—SiH(OnPr)$_2$]$_2$, Si(OiBu)$_2$[CH$_2$—SiH(OiPr)$_2$]$_2$, Si(OiBu)$_2$[CH$_2$—SiH(OnBu)$_2$]$_2$, Si(OiBu)$_2$[CH$_2$—SiH(OtBu)$_2$]$_2$, Si(OiBu)$_2$[CH$_2$—SiH(OiBu)$_2$]$_2$, Si(OSiMe$_3$)$_2$[CH$_2$—SiH(OMe)$_2$]$_2$, Si(OSiMe$_3$)$_2$[CH$_2$—SiH(OEt)$_2$]$_2$, Si(OSiMe$_3$)$_2$[CH$_2$—SiH(OiPr)$_2$]$_2$, Si(OSiMe$_3$)$_2$[CH$_2$—SiH(OnPr)$_2$]$_2$, Si(OSiMe$_3$)$_2$[CH$_2$—SiH(OnBu)$_2$]$_2$, Si(OSiMe$_3$)$_2$[CH$_2$—SiH(OtBu)$_2$]$_2$, and Si(OSiMe$_3$)$_2$[CH$_2$—SiH(OiBu)$_2$]$_2$.

Exemplary compounds wherein a=2, b=2, c=0, x=2, y=0, and z=1 include Si(OMe)$_2$[CH$_2$—SiMe(OMe)$_2$]$_2$, Si(OMe)$_2$[CH$_2$—SiMe(OEt)$_2$]$_2$, Si(OMe)$_2$[CH$_2$—SiMe(OiPr)$_2$]$_2$, Si(OMe)$_2$[CH$_2$—SiMe(OnPr)$_2$]$_2$, Si(OMe)$_2$[CH$_2$—SiMe(OnBu)$_2$]$_2$, Si(OMe)$_2$[CH$_2$—SiMe(OtBu)$_2$]$_2$, Si(OMe)$_2$[CH$_2$—SiMe(OiBu)$_2$]$_2$, Si(OEt)$_2$[CH$_2$—SiMe(OMe)$_2$]$_2$, Si(OEt)$_2$[CH$_2$—SiMe(OEt)$_2$]$_2$, Si(OEt)$_2$[CH$_2$—SiMe(OiPr)$_2$]$_2$, Si(OEt)$_2$[CH$_2$—SiMe(OnPr)$_2$]$_2$, Si(OEt)$_2$[CH$_2$—SiMe(OnBu)$_2$]$_2$, Si(OEt)$_2$[CH$_2$—SiMe(OtBu)$_2$]$_2$, Si(OEt)$_2$[CH$_2$—SiMe(OiBu)$_2$]$_2$, Si(OiPr)$_2$[CH$_2$—SiMe(OMe)$_2$]$_2$, Si(OiPr)$_2$[CH$_2$—SiMe(OEt)$_2$]$_2$, Si(OiPr)$_2$[CH$_2$—SiMe(OiPr)$_2$]$_2$, Si(OiPr)$_2$[CH$_2$—SiMe(OnPr)$_2$]$_2$, Si(OiPr)$_2$[CH$_2$—SiMe(OnBu)$_2$]$_2$, Si(OiPr)$_2$[CH$_2$—SiMe(OtBu)$_2$]$_2$, Si(OiPr)$_2$[CH$_2$—SiMe(OiBu)$_2$]$_2$, Si(OnPr)$_2$[CH$_2$—SiMe(OMe)$_2$]$_2$, Si(OnPr)$_2$[CH$_2$—SiMe(OEt)$_2$]$_2$, Si(OnPr)$_2$[CH$_2$—SiMe(OiPr)$_2$]$_2$, Si(OnPr)$_2$[CH$_2$—SiMe(OnPr)$_2$]$_2$, Si(OnPr)$_2$[CH$_2$—SiMe(OnBu)$_2$]$_2$, Si(OnPr)$_2$[CH$_2$—SiMe(OtBu)$_2$]$_2$, Si(OnPr)$_2$[CH$_2$—SiMe(OiBu)$_2$]$_2$, Si(OnBu)$_2$[CH$_2$—SiMe(OMe)$_2$]$_2$, Si(OnBu)$_2$[CH$_2$—SiMe(OEt)$_2$]$_2$, Si(OnBu)$_2$[CH$_2$—SiMe(OiPr)$_2$]$_2$, Si(OnBu)$_2$[CH$_2$—SiMe(OnPr)$_2$]$_2$, Si(OnBu)$_2$[CH$_2$—SiMe(OnBu)$_2$]$_2$, Si(OnBu)$_2$[CH$_2$—SiMe(OiBu)$_2$]$_2$, Si(OnBu)$_2$[CH$_2$—SiMe(OtBu)$_2$]$_2$, Si(OtBu)$_2$[CH$_2$—SiMe(OtBu)$_2$]$_2$, Si(OtBu)$_2$[CH$_2$—SiMe(OEtu)$_2$]$_2$, Si(OtBu)$_2$[CH$_2$—SiMe(OiPr)$_2$]$_2$, Si(OtBu)$_2$[CH$_2$—SiMe(OnPr)$_2$]$_2$, Si(OtBu)$_2$[CH$_2$—SiMe(OnBu)$_2$]$_2$, Si(OtBu)$_2$[CH$_2$—SiMe(OtBu)$_2$]$_2$, Si(OtBu)$_2$[CH$_2$—SiMe (OiBu)$_2$]$_2$, Si(OiBu)$_2$[CH$_2$—SiMe(OMe)$_2$]$_2$, Si(OiBu)$_2$[CH$_2$—SiMe(OEt)$_2$]$_2$, Si(OiBu)$_2$[CH$_2$—SiMe(OnPr)$_2$]$_2$, Si(OiBu)$_2$[CH$_2$—SiMe(OiPr)$_2$]$_2$, Si(OiBu)$_2$[CH$_2$—SiMe(OnBu)$_2$]$_2$, Si(OiBu)$_2$[CH$_2$—SiMe(OtBu)$_2$]$_2$, Si(OiBu)$_2$[CH$_2$—SiMe(OiBu)$_2$]$_2$, Si(OSiMe$_3$)$_2$[CH$_2$—SiMe(OMe)$_2$]$_2$, Si(OSiMe$_3$)$_2$[CH$_2$—SiMe(OEt)$_2$]$_2$, Si(OSiMe$_3$)$_2$[CH$_2$—SiMe(OiPr)$_2$]$_2$, Si(OSiMe$_3$)$_2$[CH$_2$—SiMe(OnPr)$_2$]$_2$, Si(OSiMe$_3$)$_2$[CH$_2$—SiMe(OnBu)$_2$]$_2$, Si(OSiMe$_3$)$_2$[CH$_2$—SiMe(OtBu)$_2$]$_2$, and Si(OSiMe$_3$)$_2$[CH$_2$—SiMe(OiBu)$_2$]$_2$.

Exemplary compounds wherein a=2, b=2, c=0, x=1, y=1, and z=1 include Si(OMe)$_2$[CH$_2$—SiHMe(OMe)]$_2$, Si(OMe)$_2$[CH$_2$—SiHMe(OEt)]$_2$, Si(OMe)$_2$[CH$_2$—SiHMe(OiPr)]$_2$, Si(OMe)$_2$[CH$_2$—SiHMe(OnPr)]$_2$, Si(OMe)$_2$[CH$_2$—SiHMe(OnBu)]$_2$, Si(OMe)$_2$[CH$_2$—SiHMe(OtBu)]$_2$, Si(OMe)$_2$[CH$_2$—SiHMe(OiBu)]$_2$, Si(OEt)$_2$[CH$_2$—SiHMe(OMe)]$_2$, Si(OEt)$_2$[CH$_2$—SiHMe(OEt)]$_2$, Si(OEt)$_2$[CH$_2$—SiHMe(OiPr)]$_2$, Si(OEt)$_2$[CH$_2$—SiHMe(OnPr)]$_2$, Si(OEt)$_2$[CH$_2$—SiHMe(OnBu)]$_2$, Si(OEt)$_2$[CH$_2$—SiHMe(OtBu)]$_2$, Si(OEt)$_2$[CH$_2$—SiHMe(OiBu)]$_2$, Si(OiPr)$_2$[CH$_2$—SiHMe(OMe)]$_2$, Si(OiPr)$_2$[CH$_2$—SiHMe(OEt)]$_2$, Si(OiPr)$_2$[CH$_2$—SiHMe(OiPr)]$_2$, Si(OiPr)$_2$[CH$_2$—SiHMe(OnPr)]$_2$, Si(OiPr)$_2$[CH$_2$—SiHMe(OnBu)]$_2$, Si(OiPr)$_2$[CH$_2$—SiHMe(OtBu)]$_2$, Si(OiPr)$_2$[CH$_2$—SiHMe(OiBu)]$_2$, Si(OnPr)$_2$[CH$_2$—SiHMe(OMe)]$_2$, Si(OnPr)$_2$[CH$_2$—SiHMe(OEt)]$_2$, Si(OnPr)$_2$[CH$_2$—SiHMe(OiPr)]$_2$, Si(OnPr)$_2$[CH$_2$—SiHMe(OnPr)]$_2$, Si(OnPr)$_2$[CH$_2$—SiHMe(OnBu)]$_2$, Si(OnPr)$_2$[CH$_2$—SiHMe(OtBu)]$_2$, Si(OnPr)$_2$[CH$_2$—SiHMe(OiBu)]$_2$, Si(OnBu)$_2$[CH$_2$—SiHMe(OMe)]$_2$, Si(OnBu)$_2$[CH$_2$—SiHMe(OEt)]$_2$, Si(OnBu)$_2$[CH$_2$—SiHMe(OiPr)]$_2$, Si(OnBu)$_2$[CH$_2$—SiHMe(OnPr)]$_2$, Si(OnBu)$_2$[CH$_2$—SiHMe(OnBu)]$_2$, Si(OnBu)$_2$[CH$_2$—SiHMe(OiBu)]$_2$, Si(OnBu)$_2$[CH$_2$—SiHMe(OtBu)]$_2$, Si(OtBu)$_2$[CH$_2$—SiHMe(OMe)]$_2$, Si(OtBu)$_2$[CH$_2$—SiHMe(OEt)]$_2$, Si(OtBu)$_2$[CH$_2$—SiHMe(OiPr)]$_2$, Si(OtBu)$_2$[CH$_2$—SiHMe(OnPr)]$_2$, Si(OtBu)$_2$[CH$_2$—SiHMe(OnBu)]$_2$, Si(OtBu)$_2$[CH$_2$—SiHMe(OtBu)]$_2$, Si(OtBu)$_2$[CH$_2$—SiHMe(OiBu)]$_2$, Si(OiBu)$_2$[CH$_2$—SiHMe(OMe)]$_2$, Si(OiBu)$_2$[CH$_2$—SiHMe(OEt)]$_2$, Si(OiBu)$_2$[CH$_2$—SiHMe(OnPr)]$_2$, Si(OiBu)$_2$[CH$_2$—SiHMe(OiPr)]$_2$, Si(OiBu)$_2$[CH$_2$—SiHMe(OnBu)]$_2$, Si(OiBu)$_2$[CH$_2$—SiHMe(OtBu)]$_2$, Si(OiBu)$_2$[CH$_2$—SiHMe(OiBu)]$_2$, Si(OSiMe$_3$)$_2$[CH$_2$—SiHMe(OMe)]$_2$, Si(OSiMe$_3$)$_2$[CH$_2$—SiHMe(OEt)]$_2$, Si(OSiMe$_3$)$_2$[CH$_2$—SiHMe(OiPr)]$_2$, Si(OSiMe$_3$)$_2$[CH$_2$—SiHMe(OnPr)]$_2$, Si(OSiMe$_3$)$_2$[CH$_2$—SiHMe(OnBu)]$_2$, Si(OSiMe$_3$)$_2$[CH$_2$—SiHMe(OtBu)]$_2$, and Si(OSiMe$_3$)$_2$[CH$_2$—SiHMe(OiBu)]$_2$.

Exemplary compounds wherein a=2, b=2, c=0, x=1, y=0, and z=2 include Si(OMe)$_2$[CH$_2$—SiMe$_2$(OMe)]$_2$, Si(OMe)$_2$[CH$_2$—SiMe$_2$(OEt)]$_2$, Si(OMe)$_2$[CH$_2$—SiMe$_2$(OiPr)]$_2$, Si(OMe)$_2$[CH$_2$—SiMe$_2$(OnPr)]$_2$, Si(OMe)$_2$[CH$_2$—SiMe$_2$(OnBu)]$_2$, Si(OMe)$_2$[CH$_2$—SiMe$_2$(OtBu)]$_2$, Si(OMe)$_2$[CH$_2$—SiMe$_2$(OiBu)]$_2$, Si(OEt)$_2$[CH$_2$—SiMe$_2$(OMe)]$_2$, Si(OEt)$_2$[CH$_2$—SiMe$_2$(OEt)]$_2$, Si(OEt)$_2$[CH$_2$—SiMe$_2$(OiPr)]$_2$, Si(OEt)$_2$[CH$_2$—SiMe$_2$(OnPr)]$_2$, Si(OEt)$_2$[CH$_2$—SiMe$_2$(OnBu)]$_2$, Si(OEt)$_2$[CH$_2$—SiMe$_2$(OtBu)]$_2$, Si(OEt)$_2$[CH$_2$—SiMe$_2$(OiBu)]$_2$, Si(OiPr)$_2$[CH$_2$—SiMe$_2$(OMe)]$_2$, Si(OiPr)$_2$[CH$_2$—SiMe$_2$(OEt)]$_2$, Si(OiPr)$_2$[CH$_2$—SiMe$_2$(OiPr)]$_2$, Si(OiPr)$_2$[CH$_2$—SiMe$_2$(OnPr)]$_2$, Si(OiPr)$_2$[CH$_2$—SiMe$_2$(OnBu)]$_2$, Si(OiPr)$_2$[CH$_2$—SiMe$_2$(OtBu)]$_2$, Si(OiPr)$_2$[CH$_2$—SiMe$_2$(OiBu)]$_2$, Si(OnPr)$_2$[CH$_2$—SiMe$_2$(OMe)]$_2$, Si(OnPr)$_2$[CH$_2$—SiMe$_2$(OEt)]$_2$, Si(OnPr)$_2$[CH$_2$—SiMe$_2$(OiPr)]$_2$, Si(OnPr)$_2$[CH$_2$—SiMe$_2$(OnPr)]$_2$, Si(OnPr)$_2$[CH$_2$—SiMe$_2$(OnBu)]$_2$, Si(OnPr)$_2$[CH$_2$—SiMe$_2$(OtBu)]$_2$, Si(OnPr)$_2$[CH$_2$—SiMe$_2$(OiBu)]$_2$, Si(OnBu)$_2$[CH$_2$—SiMe$_2$(OMe)]$_2$, Si(OnBu)$_2$[CH$_2$—SiMe$_2$(OEt)]$_2$, Si(OnBu)$_2$[CH$_2$—SiMe$_2$(OiPr)]$_2$, Si(OnBu)$_2$[CH$_2$—SiMe$_2$(OnPr)]$_2$, Si(OnBu)$_2$[CH$_2$—SiMe$_2$(OnBu)]$_2$, Si(OnBu)$_2$[CH$_2$—SiMe$_2$(OtBu)]$_2$, Si(OnBu)$_2$[CH$_2$—SiMe$_2$(OiBu)]$_2$, Si(OtBu)$_2$[CH$_2$—SiMe$_2$(OMe)]$_2$, Si(OtBu)$_2$[CH$_2$—SiMe$_2$(OEt)]$_2$, Si(OtBu)$_2$[CH$_2$—SiMe$_2$(OiPr)]$_2$, Si(OtBu)$_2$[CH$_2$—SiMe$_2$(OnPr)]$_2$, Si(OtBu)$_2$[CH$_2$—SiMe$_2$(OnBu)]$_2$, Si(OtBu)$_2$[CH$_2$—SiMe$_2$(OtBu)]$_2$, Si(OtBu)$_2$[CH$_2$—SiMe$_2$(OiBu)]$_2$, Si(OiBu)$_2$[CH$_2$—SiMe$_2$(OMe)]$_2$, Si(OiBu)$_2$[CH$_2$—SiMe$_2$(OEt)]$_2$, Si(OiBu)$_2$[CH$_2$—SiMe$_2$(OnPr)]$_2$, Si(OiBu)$_2$[CH$_2$—SiMe$_2$(OiPr)]$_2$, Si(OiBu)$_2$[CH$_2$—SiMe$_2$(OnBu)]$_2$, Si(OiBu)$_2$[CH$_2$—SiMe$_2$(OtBu)]$_2$, Si(OiBu)$_2$[CH$_2$—SiMe$_2$(OiBu)]$_2$, Si(OSiMe$_3$)$_2$[CH$_2$—SiMe$_2$(OMe)]$_2$, Si(OSiMe$_3$)$_2$[CH$_2$—SiMe$_2$(OEt)]$_2$, Si(OSiMe$_3$)$_2$[CH$_2$—SiMe$_2$(OiPr)]$_2$, Si(OSiMe$_3$)$_2$[CH$_2$—SiMe$_2$(OnPr)]$_2$, Si(OSiMe$_3$)$_2$[CH$_2$—SiMe$_2$(OnBu)]$_2$, Si(OSiMe$_3$)$_2$[CH$_2$—SiMe$_2$(OtBu)]$_2$, and Si(OSiMe$_3$)$_2$[CH$_2$—SiMe$_2$(OiBu)]$_2$.

Exemplary compounds wherein a=2, b=2, c=0, x=0, y=1, and z=2 include Si(OMe)$_2$[CH$_2$—SiHMe$_2$]$_2$, Si(OMe)$_2$[CH$_2$—SiHEt$_2$]$_2$, Si(OMe)$_2$[CH$_2$—SiH(iPr)$_2$]$_2$, Si(OMe)$_2$[CH$_2$—SiH(nPr)$_2$]$_2$, Si(OMe)$_2$[CH$_2$—SiH(nBu)$_2$]$_2$, Si(OMe)$_2$[CH$_2$—SiH(OtBu)$_2$]$_2$, Si(OMe)$_2$[CH$_2$—SiH(iBu)$_2$]$_2$, Si(OMe)$_2$[CH$_2$—SiH(SiMe$_3$)$_2$]$_2$, Si(OEt)$_2$[CH$_2$—SiHMe$_2$]$_2$, Si(OEt)$_2$[CH$_2$—SiHEt$_2$]$_2$, Si(OEt)$_2$[CH$_2$—SiH(iPr)$_2$]$_2$, Si(OEt)$_2$[CH$_2$—SiH(nPr)$_2$]$_2$, Si(OEt)$_2$[CH$_2$—SiH(nBu)$_2$]$_2$, Si(OEt)$_2$[CH$_2$—SiH(OtBu)$_2$]$_2$, Si(OEt)$_2$[CH$_2$—SiH(iBu)$_2$]$_2$, Si(OEt)$_2$[CH$_2$—SiH(SiMe$_3$)$_2$]$_2$, Si(OiPr)$_2$[CH$_2$—SiHMe$_2$]$_2$, Si(OiPr)$_2$[CH$_2$—SiHEt$_2$]$_2$, Si(OiPr)$_2$[CH$_2$—SiH(iPr)$_2$]$_2$, Si(OiPr)$_2$[CH$_2$—SiH(nPr)$_2$]$_2$, Si(OiPr)$_2$[CH$_2$—SiH(nBu)$_2$]$_2$, Si(OiPr)$_2$[CH$_2$—SiH(OtBu)$_2$]$_2$, Si(OiPr)$_2$[CH$_2$—SiH(iBu)$_2$]$_2$, Si(OiPr)$_2$[CH$_2$—SiH(SiMe$_3$)$_2$]$_2$, Si(OnPr)$_2$[CH$_2$—SiHMe$_2$]$_2$, Si(OnPr)$_2$[CH$_2$—SiHEt$_2$]$_2$, Si(OnPr)$_2$[CH$_2$—SiH(iPr)$_2$]$_2$, Si(OnPr)$_2$[CH$_2$—SiH(nPr)$_2$]$_2$, Si(OnPr)$_2$[CH$_2$—SiH(nBu)$_2$]$_2$, Si(OnPr)$_2$[CH$_2$—SiH(OtBu)$_2$]$_2$, Si(OnPr)$_2$[CH$_2$—SiH(iBu)$_2$]$_2$, Si(OnPr)$_2$[CH$_2$—SiH(SiMe$_3$)$_2$]$_2$, Si(OnBu)$_2$[CH$_2$—SiHMe$_2$]$_2$, Si(OnBu)$_2$[CH$_2$—SiHEt$_2$]$_2$, Si(OnBu)$_2$[CH$_2$—SiH(iPr)$_2$]$_2$, Si(OnBu)$_2$[CH$_2$—SiH(nPr)$_2$]$_2$, Si(OnBu)$_2$[CH$_2$—SiH(nBu)$_2$]$_2$, Si(OnBu)$_2$[CH$_2$—SiH(OtBu)$_2$]$_2$, Si(OnBu)$_2$[CH$_2$—SiH(iBu)$_2$]$_2$, Si(OnBu)$_2$[CH$_2$—SiH(SiMe$_3$)$_2$]$_2$, Si(OiBu)$_2$[CH$_2$—SiHMe$_2$]$_2$, Si(OiBu)$_2$[CH$_2$—SiHEt$_2$]$_2$, Si(OiBu)$_2$[CH$_2$—SiH(iPr)$_2$]$_2$, Si(OiBu)$_2$[CH$_2$—SiH(nPr)$_2$]$_2$, Si(OiBu)$_2$[CH$_2$—SiH(nBu)$_2$]$_2$, Si(OiBu)$_2$[CH$_2$—SiH(OtBu)$_2$]$_2$, Si(OiBu)$_2$[CH$_2$—SiH(iBu)$_2$]$_2$, Si(OiBu)$_2$[CH$_2$—SiH(SiMe$_3$)$_2$]$_2$, Si(OtBu)$_2$[CH$_2$—SiHMe$_2$]$_2$, Si(OtBu)$_2$[CH$_2$—SiHEt$_2$]$_2$, Si(OtBu)$_2$[CH$_2$—SiH(iPr)$_2$]$_2$, Si(OtBu)$_2$[CH$_2$—SiH(nPr)$_2$]$_2$, Si(OtBu)$_2$[CH$_2$—SiH(nBu)$_2$]$_2$, Si(OtBu)$_2$[CH$_2$—SiH(OtBu)$_2$]$_2$, Si(OtBu)$_2$[CH$_2$—SiH(iBu)$_2$]$_2$, Si(OtBu)$_2$[CH$_2$—SiH(SiMe$_3$)$_2$]$_2$, Si(OSiMe$_3$)$_2$[CH$_2$—SiHMe$_2$]$_2$, Si(OSiMe$_3$)$_2$[CH$_2$—SiHEt$_2$]$_2$, Si(OSiMe$_3$)$_2$[CH$_2$—SiH(iPr)$_2$]$_2$, Si(OSiMe$_3$)$_2$[CH$_2$—SiH(nPr)$_2$]$_2$, Si(OSiMe$_3$)$_2$[CH$_2$—SiH(nBu)$_2$]$_2$, Si(OSiMe$_3$)$_2$[CH$_2$—SiH(OtBu)$_2$]$_2$, Si(OSiMe$_3$)$_2$[CH$_2$—SiH(iBu)$_2$]$_2$, and Si(OSiMe$_3$)$_2$[CH$_2$—SiH(SiMe$_3$)$_2$]$_2$.

Exemplary compounds wherein a=2, b=2, c=0, x=0, y=0, and z=3 include Si(OMe)$_2$[CH$_2$—SiMe$_3$]$_2$, Si(OMe)$_2$[CH$_2$—SiEt$_3$]$_2$, Si(OMe)$_2$[CH$_2$—Si(iPr)$_3$]$_2$, Si(OMe)$_2$[CH$_2$—Si(nPr)$_3$]$_2$, Si(OMe)$_2$[CH$_2$—Si(nBu)$_3$]$_2$, Si(OMe)$_2$[CH$_2$—Si(OtBu)$_3$]$_2$, Si(OMe)$_2$[CH$_2$—Si(iBu)$_3$]$_2$, Si(OMe)$_2$[CH$_2$—Si(SiMe$_3$)$_3$]$_2$, Si(OEt)$_2$[CH$_2$—SiMe$_3$]$_2$, Si(OEt)$_2$[CH$_2$—SiEt$_3$]$_2$, Si(OEt)$_2$[CH$_2$—Si(iPr)$_3$]$_2$, Si(OEt)$_2$[CH$_2$—SiH(nPr)$_3$]$_2$, Si(OEt)$_2$[CH$_2$—Si(nBu)$_3$]$_2$, Si(OEt)$_2$[CH$_2$—Si(OtBu)$_3$]$_2$, Si(OEt)$_2$[CH$_2$—Si(iBu)$_3$]$_2$, Si(OEt)$_2$[CH$_2$—Si(SiMe$_3$)$_3$]$_2$, Si(OiPr)$_2$—[CH$_2$—SiMe$_3$]$_2$, Si(OiPr)$_2$[CH$_2$—SiEt$_3$]$_2$, Si(OiPr)$_2$[CH$_2$—Si(iPr)$_3$]$_2$, Si(OiPr)$_2$[CH$_2$—Si(nPr)$_3$]$_2$, Si(OiPr)$_2$[CH$_2$—Si(nBu)$_3$]$_2$, Si(OiPr)$_2$[CH$_2$—Si(OtBu)$_3$]$_2$, Si(OiPr)$_2$[CH$_2$—Si(iBu)$_3$]$_2$, Si(OiPr)$_2$[CH$_2$—Si(SiMe$_3$)$_3$]$_2$, Si(OnPr)$_2$[CH$_2$—SiMe$_3$]$_2$, Si(OnPr)$_2$[CH$_2$—SiEt$_3$]$_2$, Si(OnPr)$_2$[CH$_2$—Si(iPr)$_3$]$_2$, Si(OnPr)$_2$[CH$_2$—Si(nPr)$_3$]$_2$, Si(OnPr)$_2$[CH$_2$—Si(nBu)$_3$]$_2$, Si(OnPr)$_2$[CH$_2$—Si(OtBu)$_3$]$_2$, Si(OnPr)$_2$[CH$_2$—Si(iBu)$_3$]$_2$, Si(OnPr)$_2$[CH$_2$—Si (SiMe$_3$)$_3$]$_2$, Si(OnBu)$_2$[CH$_2$—SiMe$_3$]$_2$, Si(OnBu)$_2$[CH$_2$—SiEt$_3$]$_2$, Si(OnBu)$_2$[CH$_2$—Si(iPr)$_3$]$_2$, Si(OnBu)$_2$[CH$_2$—Si(nPr)$_3$]$_2$, Si(OnBu)$_2$[CH$_2$—Si(nBu)$_3$]$_2$, Si(OnBu)$_2$[CH$_2$—Si(OtBu)$_3$]$_2$, Si(OnBu)$_2$[CH$_2$—Si(iBu)$_3$]$_2$, Si(OnBu)$_2$[CH$_2$—Si(SiMe$_3$)$_3$]$_2$, Si(OiBu)$_2$[CH$_2$—SiMe$_3$]$_2$, Si(OiBu)$_2$[CH$_2$—SiEt$_3$]$_2$, Si(OiBu)$_2$[CH$_2$—Si(iPr)$_3$]$_2$, Si(OiBu)$_2$[CH$_2$—Si(nPr)$_3$]$_2$, Si(OiBu)$_2$[CH$_2$—Si(nBu)$_3$]$_2$, Si(OiBu)$_2$[CH$_2$—SiH(OtBu)$_2$]$_2$, Si(OiBu)$_2$[CH$_2$—Si(iBu)$_3$]$_2$, Si(OiBu)$_2$[CH$_2$—Si(SiMe$_3$)$_3$]$_2$, Si(OtBu)$_2$[CH$_2$—SiMe$_3$]$_2$, Si(OtBu)$_2$[CH$_2$—SiEt$_3$]$_2$, Si(OtBu)$_2$[CH$_2$—Si(iPr)$_3$]$_2$, Si(OtBu)$_2$[CH$_2$—Si(nPr)$_3$]$_2$, Si(OtBu)$_2$[CH$_2$—Si(nBu)$_3$]$_2$, Si(OtBu)$_2$[CH$_2$—Si(OtBu)$_3$]$_2$, Si(OtBu)$_2$[CH$_2$—Si(iBu)$_3$]$_2$, Si(OtBu)$_2$[CH$_2$—Si(SiMe$_3$)$_3$]$_2$, Si(OSiMe$_3$)$_2$[CH$_2$—SiMe$_3$]$_2$, Si(OSiMe$_3$)$_2$[CH$_2$—SiEt$_3$]$_2$, Si(OSiMe$_3$)$_2$[CH$_2$—Si(iPr)$_3$]$_2$, Si(OSiMe$_3$)$_2$[CH$_2$—Si(nPr)$_3$]$_2$, Si(OSiMe$_3$)$_2$[CH$_2$—Si(nBu)$_3$]$_2$, Si(OSiMe$_3$)$_2$[CH$_2$—Si(OtBu)$_3$]$_2$, Si(OSiMe$_3$)$_2$[CH$_2$—Si(iBu)$_3$]$_2$, and Si(OSiMe$_3$)$_2$[CH$_2$—Si(SiMe$_3$)$_3$]$_2$.

In some embodiments, y=1 and b=0 to produce Si(H)$_c$[CH$_2$—Si(OR')$_x$HR$_{2-x}$]$_a$, wherein a=1 to 3; c=0 to 2; a+c=4; x=0 to 2; each R is independently a C1 to C5 linear or branched alkyl group or a trimethylsilyl group; and each R' is independently a C1 to C5 linear or branched alkyl group.

Exemplary compounds wherein y=1, b=0, a=3, c=1, x=2, and z=0 include SiH[CH$_2$—SiH(OMe)$_2$]$_3$, SiH[CH$_2$—SiH(OEt)$_2$]$_3$, SiH[CH$_2$—SiH(OiPr)$_2$]$_3$, SiH[CH$_2$—SiH(OnPr)$_2$]$_3$, SiH[CH$_2$—SiH(OnBu)$_2$]$_3$, SiH[CH$_2$—SiH(OtBu)$_2$]$_3$, and SiH[CH$_2$—SiH(OiBu)$_2$]$_3$.

Exemplary compounds wherein y=1, b=0, a=3, c=1, x=0, and z=2 include SiH[CH$_2$—SiH(Me)$_2$]$_3$, SiH[CH$_2$—SiH(Et)$_2$]$_3$, SiH[CH$_2$—SiH(iPr)$_2$]$_3$, SiH[CH$_2$—SiH(nPr)$_2$]$_3$, SiH[CH$_2$—SiH(nBu)$_2$]$_3$, SiH[CH$_2$—SiH(tBu)$_2$]$_3$, SiH[CH$_2$—SiH(iBu)$_2$]$_3$, and SiH[CH$_2$—SiH(SiMe$_3$)$_2$]$_3$.

Exemplary compounds wherein y=1, b=0, a=3, c=1, x=1, and z=1 include SiH[CH$_2$—SiH(Me)(OMe)]$_3$, SiH[CH$_2$—SiH(Me)(OEt)]$_3$, SiH[CH$_2$—SiH(Me)(OiPr)]$_3$, SiH[CH$_2$—SiH(Me)(OnPr)]$_3$, SiH[CH$_2$—SiH(Me)(OnBu)]$_3$, SiH[CH$_2$—SiH(Me)(OtBu)]$_3$, SiH[CH$_2$—SiH(Me)(OiBu)]$_3$, SiH[CH$_2$—SiH(Et)(OMe)]$_3$, SiH[CH$_2$—SiH(Et)(OEt)]$_3$, SiH[CH$_2$—SiH(Et)(OiPr)]$_3$, SiH[CH$_2$—SiH(Et)(OnPr)]$_3$, SiH[CH$_2$—SiH(Et)(OnBu)]$_3$, SiH[CH$_2$—SiH(Et)(OtBu)]$_3$, SiH[CH$_2$—SiH(Et)(OiBu)]$_3$, SiH[CH$_2$—SiH(iPr)(OMe)]$_3$, SiH[CH$_2$—SiH(iPr)(OEt)]$_3$, SiH[CH$_2$—SiH(iPr)(OiPr)]$_3$, SiH[CH$_2$—SiH(iPr)(OnPr)]$_3$, SiH[CH$_2$—SiH(iPr)(OnBu)]$_3$, SiH[CH$_2$—SiH(iPr)(OtBu)]$_3$, SiH[CH$_2$—SiH(iPr)(OiBu)]$_3$, SiH[CH$_2$—SiH(nPr)(OMe)]$_3$, SiH[CH$_2$—SiH(nPr)(OEt)]$_3$, SiH[CH$_2$—SiH(nPr)(OiPr)]$_3$, SiH[CH$_2$—SiH(nPr)(OnPr)]$_3$, SiH[CH$_2$—SiH(nPr)(OnBu)]$_3$, SiH[CH$_2$—SiH(nPr)(OtBu)]$_3$, SiH[CH$_2$—SiH(nPr)(OiBu)]$_3$, SiH[CH$_2$—SiH(nBu)(OMe)]$_3$, SiH[CH$_2$—SiH(nBu)(OEt)]$_3$, SiH[CH$_2$—SiH(nBu)(OiPr)]$_3$, SiH[CH$_2$—SiH(nBu)(OnPr)]$_3$, SiH[CH$_2$—SiH(nBu)(OnBu)]$_3$, SiH[CH$_2$—SiH(nBu)(OtBu)]$_3$, SiH[CH$_2$—SiH(nBu)(OiBu)]$_3$, SiH[CH$_2$—SiH(tBu)(OMe)]$_3$, SiH[CH$_2$—SiH(tBu)(OEt)]$_3$, SiH[CH$_2$—SiH(tBu)(OiPr)]$_3$, SiH[CH$_2$—SiH(tBu)(OnPr)]$_3$, SiH[CH$_2$—SiH(tBu)(OnBu)]$_3$, SiH[CH$_2$—SiH(tBu)(OtBu)]$_3$, SiH[CH$_2$—SiH(tBu)(OiBu)]$_3$, SiH[CH$_2$—SiH(iBu)(OMe)]$_3$, SiH[CH$_2$—SiH(iBu)(OEt)]$_3$, SiH[CH$_2$—SiH(iBu)(OiPr)]$_3$, SiH[CH$_2$—SiH(iBu)(OnPr)]$_3$, SiH[CH$_2$—SiH(iBu)(OnBu)]$_3$, SiH[CH$_2$—SiH(iBu)(OtBu)]$_3$, SiH[CH$_2$—SiH(iBu)(OiBu)]$_3$, SiH[CH$_2$—SiH(SiMe$_3$)(OMe)]$_3$, SiH[CH$_2$—SiH(SiMe$_3$)(OEt)]$_3$, SiH[CH$_2$—SiH(SiMe$_3$)(OiPr)]$_3$, SiH[CH$_2$—SiH(SiMe$_3$)(OnPr)]$_3$, SiH[CH$_2$—SiH(SiMe$_3$)(OnBu)]$_3$, SiH[CH$_2$—SiH(SiMe$_3$)(OtBu)]$_3$, and SiH[CH$_2$—SiH(SiMe$_3$)(OiBu)]$_3$.

Exemplary compounds wherein y=1, b=0, a=2, c=2, x=2, and z=0 include SiH$_2$—[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, and SiH$_2$[CH$_2$—SiH(OiBu)$_2$]$_2$.

Exemplary compounds wherein y=1, b=0, a=2, c=2, x=0, and z=2 include SiH$_2$[CH$_2$—SiH(Me)$_2$]$_2$, SiH$_2$[CH$_2$—SiH(Et)$_2$]$_2$, SiH$_2$[CH$_2$—SiH(iPr)$_2$]$_2$, SiH$_2$[CH$_2$—SiH(nPr)$_2$]$_2$, SiH$_2$[CH$_2$—SiH(nBu)$_2$]$_2$, SiH$_2$[CH$_2$—SiH(tBu)$_2$]$_2$, SiH$_2$[CH$_2$—SiH(iBu)$_2$]$_2$, and SiH$_2$[CH$_2$—SiH(SiMe$_3$)$_2$]$_2$.

Exemplary compounds wherein y=1, b=0, a=2, c=2, x=1, and z=1 include SiH$_2$[CH$_2$—SiH(Me)(OMe)]$_2$, SiH$_2$[CH$_2$—SiH(Me)(OEt)]$_2$, SiH$_2$[CH$_2$—SiH(Me)(OiPr)]$_2$, SiH$_2$[CH$_2$—SiH(Me)(OnPr)]$_2$, SiH$_2$[CH$_2$—SiH(Me)(OnBu)]$_2$, SiH$_2$[CH$_2$—SiH(Me)(OiBu)]$_2$, SiH$_2$[CH$_2$—SiH(Me)(OtBu)]$_2$, SiH$_2$[CH$_2$—SiH(Et)(OMe)]$_2$, SiH$_2$[CH$_2$—SiH(Et)(OEt)]$_2$, SiH$_2$[CH$_2$—SiH(Et)(OiPr)]$_2$, SiH$_2$[CH$_2$—SiH(Et)(OnPr)]$_2$, SiH$_2$[CH$_2$—SiH(Et)(OnBu)]$_2$, SiH$_2$[CH$_2$—SiH(Et)(OtBu)]$_2$, SiH$_2$[CH$_2$—SiH(Et)(OiBu)]$_2$, SiH$_2$[CH$_2$—SiH(iPr)(OMe)]$_2$, SiH$_2$[CH$_2$—SiH(iPr)(OEt)]$_2$, SiH$_2$[CH$_2$—SiH(iPr)(OiPr)]$_2$, SiH$_2$[CH$_2$—SiH(iPr)(OnPr)]$_2$, SiH$_2$[CH$_2$—SiH(iPr)(OnBu)]$_2$, SiH$_2$[CH$_2$—SiH(iPr)(OtBu)]$_2$, SiH$_2$[CH$_2$—SiH(iPr)(OiBu)]$_2$, SiH$_2$[CH$_2$—SiH(nPr)(OMe)]$_2$, SiH$_2$[CH$_2$—SiH(nPr)(OEt)]$_2$, SiH$_2$[CH$_2$—SiH(nPr)(OnPr)]$_2$, SiH$_2$[CH$_2$—SiH(nPr)(OiPr)]$_2$, SiH$_2$[CH$_2$—SiH(nPr)(OnBu)]$_2$, SiH$_2$[CH$_2$—SiH(nPr)(OtBu)]$_2$, SiH$_2$[CH$_2$—SiH(nPr)(OiBu)]$_2$, SiH$_2$[CH$_2$—SiH(nBu)(OMe)]$_2$, SiH$_2$[CH$_2$—SiH(nBu)(OEt)]$_2$, SiH$_2$[CH$_2$—SiH(nBu)(OnPr)]$_2$, SiH$_2$[CH$_2$—SiH(nBu)(OiPr)]$_2$, SiH$_2$[CH$_2$—SiH(nBu)(OnBu)]$_2$, SiH$_2$[CH$_2$—SiH(nBu)(OtBu)]$_2$, SiH$_2$[CH$_2$—SiH(nBu)(OiBu)]$_2$, SiH$_2$[CH$_2$—SiH(tBu)(OMe)]$_2$, SiH$_2$[CH$_2$—SiH(tBu)(OEt)]$_2$, SiH$_2$[CH$_2$—SiH(tBu)(OnPr)]$_2$, SiH$_2$[CH$_2$—SiH(tBu)(OiPr)]$_2$, SiH$_2$[CH$_2$—SiH(tBu)(OnBu)]$_2$, SiH$_2$[CH$_2$—SiH(tBu)(OtBu)]$_2$, SiH$_2$[CH$_2$—SiH(tBu)(OiBu)]$_2$, SiH$_2$[CH$_2$—SiH(iBu)(OMe)]$_2$, SiH$_2$[CH$_2$—SiH(iBu)(OEt)]$_2$, SiH$_2$[CH$_2$—SiH(iBu)(OnPr)]$_2$, SiH$_2$[CH$_2$—SiH(iBu)(OiPr)]$_2$, SiH$_2$[CH$_2$—SiH(iBu)(OnBu)]$_2$, SiH$_2$[CH$_2$—SiH(iBu)(OtBu)]$_2$, SiH$_2$[CH$_2$—SiH(iBu)(OiBu)]$_2$, SiH$_2$[CH$_2$—SiH(SiMe$_3$)(OMe)]$_2$, SiH$_2$-[CH$_2$—SiH(SiMe$_3$)(OEt)]$_2$, SiH$_2$[CH$_2$—SiH(SiMe$_3$)(OnPr)]$_2$, SiH$_2$[CH$_2$—SiH(SiMe$_3$)(OiPr)]$_2$, SiH$_2$[CH$_2$—SiH(SiMe$_3$)(OnBu)]$_2$, SiH$_2$[CH$_2$—SiH(SiMe$_3$)(OtBu)]$_2$, and SiH$_2$[CH$_2$—SiH(SiMe$_3$)(OiBu)]$_2$.

In some embodiments, z=0 and c=2 to produce Si(OR)$_{2-a}$H$_2$[CH$_2$—Si(OR')$_{3-y}$H$_y$]$_a$, wherein a=1 to 2; y=0 to 1; each R is independently a C1 to C5 linear or branched alkyl group or a trimethylsilyl group; and each R' is independently a C1 to C5 linear or branched alkyl group.

Exemplary compounds wherein z=0, c=2, a=2, and y=1 include SiH$_2$[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, SiH$_2$[CH$_2$—SiH(OiBu)$_2$]$_2$, Exemplary compounds wherein z=0, c=2, a=2, and y=0 include SiH$_2$[CH$_2$—Si(OMe)$_3$]$_2$, SiH$_2$[CH$_2$—Si (OEt)$_3$]$_2$, SiH$_2$[CH$_2$—Si(OiPr)$_3$]$_2$, SiH$_2$[CH$_2$—Si(OnPr)$_3$]$_2$, SiH$_2$[CH$_2$—Si(OnBu)$_3$]$_2$, SiH$_2$[CH$_2$—Si(OtBu)$_3$]$_2$, SiH$_2$[CH$_2$—Si(OiBu)$_3$]$_2$, Exemplary compounds wherein z=0, c=2, a=1, and y=1 include Si(OMe)H$_2$[CH$_2$—SiH(OMe)$_2$], Si(OMe)H$_2$[CH$_2$—SiH(OEt)$_2$], Si(OMe)H$_2$[CH$_2$—SiH(OiPr)$_2$], Si(OMe)H$_2$[CH$_2$—SiH(OnPr)$_2$], Si(OMe)H$_2$[CH$_2$—SiH(OnBu)$_2$], Si(OMe)H$_2$[CH$_2$—SiH(OtBu)$_2$], Si(OMe)H$_2$[CH$_2$—SiH(OiBu)$_2$], Si(OEt)H$_2$[CH$_2$—SiH(OMe)$_2$], Si(OEt)H$_2$[CH$_2$—SiH(OEt)$_2$], Si(OEt)H$_2$[CH$_2$—SiH(OiPr)$_2$], Si(OEt)H$_2$[CH$_2$—SiH(OnPr)$_2$], Si(OEt)H$_2$[CH$_2$—SiH(OnBu)$_2$], Si(OEt)H$_2$[CH$_2$—SiH(OtBu)$_2$], Si(OEt)H$_2$[CH$_2$—SiH(OiBu)$_2$], Si(OiPr)H$_2$[CH$_2$—SiH(OMe)$_2$], Si(OiPr)H$_2$[CH$_2$—SiH(OEt)$_2$], Si(OiPr)H$_2$[CH$_2$—SiH(OiPr)$_2$], Si(OiPr)H$_2$[CH$_2$—SiH(OnPr)$_2$], Si(OiPr)H$_2$

[CH$_2$—SiH(OnBu)$_2$], Si(OiPr)H$_2$[CH$_2$—SiH(OtBu)$_2$], Si(OiPr)H$_2$[CH$_2$—SiH(OiBu)$_2$], Si(OnPr)H$_2$[CH$_2$—SiH(OMe)$_2$], Si(OnPr)H$_2$[CH$_2$—SiH(OEt)$_2$], Si(OnPr)H$_2$[CH$_2$—SiH(OiPr)$_2$], Si(OnPr)H$_2$[CH$_2$—SiH(OnPr)$_2$], Si(OnPr)H$_2$[CH$_2$—SiH(OnBu)$_2$], Si(OnPr)H$_2$[CH$_2$—SiH(OtBu)$_2$], Si(OnPr)H$_2$[CH$_2$—SiH(OiBu)$_2$], Si(OnBu)H$_2$[CH$_2$—SiH(OMe)$_2$], Si(OnBu)H$_2$[CH$_2$—SiH(OEt)$_2$], Si(OnBu)H$_2$[CH$_2$—SiH(OiPr)$_2$], Si(OnBu)H$_2$[CH$_2$—SiH(OnPr)$_2$], Si(OnBu)H$_2$[CH$_2$—SiH(OnBu)$_2$], Si(OnBu)H$_2$[CH$_2$—SiH(OtBu)$_2$], Si(OnBu)H$_2$[CH$_2$—SiH(OiBu)$_2$], Si(OtBu)H$_2$[CH$_2$—SiH(OMe)$_2$], Si(OtBu)H$_2$[CH$_2$—SiH(OEt)$_2$], Si(OtBu)H$_2$[CH$_2$—SiH(OiPr)$_2$], Si(OtBu)H$_2$[CH$_2$—SiH(OnPr)$_2$], Si(OtBu)H$_2$[CH$_2$—SiH(OnBu)$_2$], Si(OtBu)H$_2$[CH$_2$—SiH(OtBu)$_2$], Si(OtBu)H$_2$[CH$_2$—SiH(OiBu)$_2$], Si(OiBu)H$_2$[CH$_2$—SiH(OMe)$_2$], Si(OiBu)H$_2$[CH$_2$—SiH(OEt)$_2$], Si(OiBu)H$_2$[CH$_2$—SiH(OiPr)$_2$], Si(OiBu)H$_2$[CH$_2$—SiH(OnPr)$_2$], Si(OiBu)H$_2$[CH$_2$—SiH(OnBu)$_2$], Si(OiBu)H$_2$[CH$_2$—SiH(OtBu)$_2$], Si(OiBu)H$_2$[CH$_2$—SiH(OiBu)$_2$], Si(OSiMe$_3$)H$_2$[CH$_2$—SiH(OMe)$_2$], Si(OSiMe$_3$)H$_2$[CH$_2$—SiH(OEt)$_2$], Si(OSiMe$_3$)H$_2$[CH$_2$—SiH(OiPr)$_2$], Si(OSiMe$_3$)H$_2$[CH$_2$—SiH(OnPr)$_2$], Si(OSiMe$_3$)H$_2$[CH$_2$—SiH(OnBu)$_2$], Si(OSiMe$_3$)H$_2$[CH$_2$—SiH(OtBu)$_2$], Si(OSiMe$_3$)H$_2$[CH$_2$—SiH(OiBu)$_2$].

Exemplary compounds wherein z=0, c=2, a=1, and y=0 include Si(OMe)H$_2$[CH$_2$—Si(OMe)$_3$], Si(OMe)H$_2$[CH$_2$—Si(OEt)$_3$], Si(OMe)H$_2$[CH$_2$—Si(OiPr)$_3$], Si(OMe)H$_2$[CH$_2$—Si(OnPr)$_3$], Si(OMe)H$_2$[CH$_2$—Si(OnBu)$_3$], Si(OMe)H$_2$[CH$_2$—Si(OtBu)$_3$], Si(OMe)H$_2$[CH$_2$—Si(OiBu)$_3$], Si(OEt)H$_2$[CH$_2$—Si(OMe)$_3$], Si(OEt)H$_2$[CH$_2$—Si(OEt)$_3$], Si(OEt)H$_2$[CH$_2$—Si(OiPr)$_3$], Si(OEt)H$_2$[CH$_2$—Si(OnPr)$_3$], Si(OEt)H$_2$[CH$_2$—Si(OnBu)$_3$], Si(OEt)H$_2$[CH$_2$—Si(OtBu)$_3$], Si(OEt)H$_2$[CH$_2$—Si(OiBu)$_3$], Si(OiPr)H$_2$[CH$_2$—Si(OMe)$_3$], Si(OiPr)H$_2$[CH$_2$—Si(OEt)$_3$], Si(OiPr)H$_2$[CH$_2$—Si(OiPr)$_3$], Si(OiPr)H$_2$[CH$_2$—Si(OnPr)$_3$], Si(OiPr)H$_2$[CH$_2$—Si(OnBu)$_3$], Si(OiPr)H$_2$[CH$_2$—Si(OtBu)$_3$], Si(OiPr)H$_2$[CH$_2$—Si(OiBu)$_3$], Si(OnPr)H$_2$[CH$_2$—Si(OMe)$_3$], Si(OnPr)H$_2$[CH$_2$—Si(OEt)$_3$], Si(OnPr)H$_2$[CH$_2$—Si(OiPr)$_3$], Si(OnPr)H$_2$[CH$_2$—Si(OnPr)$_3$], Si(OnPr)H$_2$[CH$_2$—Si(OnBu)$_3$], Si(OnPr)H$_2$[CH$_2$—Si(OtBu)$_3$], Si(OnPr)H$_2$[CH$_2$—Si(OiBu)$_3$], Si(OnBu)H$_2$[CH$_2$—Si(OMe)$_3$], Si(OnBu)H$_2$[CH$_2$—Si(OEt)$_3$], Si(OnBu)H$_2$[CH$_2$—Si(OiPr)$_3$], Si(OnBu)H$_2$[CH$_2$—Si(OnPr)$_3$], Si(OnBu)H$_2$[CH$_2$—Si(OnBu)$_3$], Si(OnBu)H$_2$[CH$_2$—Si(OtBu)$_3$], Si(OnBu)H$_2$[CH$_2$—Si(OiBu)$_3$], Si(OtBu)H$_2$[CH$_2$—Si(OMe)$_3$], Si(OtBu)H$_2$[CH$_2$—Si(OEt)$_3$], Si(OtBu)H$_2$[CH$_2$—Si(OiPr)$_3$], Si(OtBu)H$_2$[CH$_2$—Si(OnPr)$_3$], Si(OtBu)H$_2$[CH$_2$—Si(OnBu)$_3$], Si(OtBu)H$_2$[CH$_2$—Si(OtBu)$_3$], Si(OtBu)H$_2$[CH$_2$—Si(OiBu)$_3$], Si(OiBu)H$_2$[CH$_2$—Si(OMe)$_3$], Si(OiBu)H$_2$[CH$_2$—Si(OEt)$_3$], Si(OiBu)H$_2$[CH$_2$—Si(OiPr)$_3$], Si(OiBu)H$_2$[CH$_2$—Si(OnPr)$_3$], Si(OiBu)H$_2$[CH$_2$—Si(OnBu)$_3$], Si(OiBu)H$_2$[CH$_2$—Si(OtBu)$_3$], Si(OiBu)H$_2$[CH$_2$—Si(OiBu)$_3$], Si(OSiMe$_3$)H$_2$[CH$_2$—Si(OMe)$_3$], Si(OSiMe$_3$)H$_2$[CH$_2$—Si(OEt)$_3$], Si(OSiMe$_3$)H$_2$[CH$_2$—Si(OiPr)$_3$], Si(OSiMe$_3$)H$_2$[CH$_2$—Si(OnPr)$_3$], Si(OSiMe$_3$)H$_2$[CH$_2$—Si(OnBu)$_3$], Si(OSiMe$_3$)H$_2$[CH$_2$—Si(OtBu)$_3$], and Si(OSiMe$_3$)H$_2$[CH$_2$—Si(OiBu)$_3$].

In some embodiments, b=0 and c=2 to produce SiH$_2$[CH$_2$—Si(OR')$_x$H$_y$R$_z$]$_2$, wherein x=0 to 3; y=0-1; z=0-3; each R is independently a C1 to C5 linear or branched alkyl group or a trimethylsilyl group; and each R' is independently a C1 to C5 linear or branched alkyl group.

Exemplary compounds wherein b=0, c=2, x=3, y=0, and z=0 include SiH$_2$[CH$_2$—Si(OMe)$_3$]$_2$, SiH$_2$[CH$_2$—Si(OEt)$_3$]$_2$, SiH$_2$[CH$_2$—Si(OiPr)$_3$]$_2$, SiH$_2$[CH$_2$—Si(OnPr)$_3$]$_2$, SiH$_2$[CH$_2$—Si(OnBu)$_3$]$_2$, SiH$_2$[CH$_2$—Si(OtBu)$_3$]$_2$, and SiH$_2$[CH$_2$—Si(OiBu)$_3$]$_2$.

Exemplary compounds wherein b=0, c=2, x=0, y=0, and z=3 include SiH$_2$[CH$_2$—Si(Me)$_3$]$_2$, SiH$_2$[CH$_2$—Si(Et)$_3$]$_2$, SiH$_2$[CH$_2$—Si(iPr)$_3$]$_2$, SiH$_2$[CH$_2$—Si(nPr)$_3$]$_2$, SiH$_2$[CH$_2$—Si(nBu)$_3$]$_2$, SiH$_2$[CH$_2$—Si(tBu)$_3$]$_2$, SiH$_2$[CH$_2$—Si(iBu)$_3$]$_2$, and SiH$_2$[CH$_2$—Si(SiMe$_3$)$_3$]$_2$.

Exemplary compounds wherein b=0, c=2, x=2, y=1, and z=0 include SiH$_2$[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, SiH$_2$[CH$_2$—SiH(OiBu)$_2$]$_2$.

Exemplary compounds wherein b=0, c=2, x=0, y=1, and z=2 include SiH$_2$[CH$_2$—SiH(Me)$_2$]$_2$, SiH$_2$[CH$_2$—SiH(Et)$_2$]$_2$, SiH$_2$[CH$_2$—SiH(iPr)$_2$]$_2$, SiH$_2$[CH$_2$—SiH(nPr)$_2$]$_2$, SiH$_2$[CH$_2$—SiH(nBu)$_2$]$_2$, SiH$_2$[CH$_2$—SiH(tBu)$_2$]$_2$, SiH$_2$[CH$_2$—SiH(iBu)$_2$]$_2$, SiH$_2$[CH$_2$—SiH(SiMe$_3$)$_2$]$_2$.

Exemplary compounds wherein b=0, c=2, x=1, y=1, and z=1 include SiH$_2$[CH$_2$—SiH(Me)(OMe)]$_2$, SiH$_2$[CH$_2$—SiH(Me)(OEt)]$_2$, SiH$_2$[CH$_2$—SiH(Me)(OiPr)]$_2$, SiH$_2$[CH$_2$—SiH(Me)(OnPr)]$_2$, SiH$_2$[CH$_2$—SiH(Me)(OnBu)]$_2$, SiH$_2$[CH$_2$—SiH(Me)(OiBu)]$_2$, SiH$_2$[CH$_2$—SiH(Me)(OtBu)]$_2$, SiH$_2$[CH$_2$—SiH(Et)(OMe)]$_2$, SiH$_2$[CH$_2$—SiH(Et)(OEt)]$_2$, SiH$_2$[CH$_2$—SiH(Et)(OiPr)]$_2$, SiH$_2$[CH$_2$—SiH(Et)(OnPr)]$_2$, SiH$_2$[CH$_2$—SiH(Et)(OnBu)]$_2$, SiH$_2$[CH$_2$—SiH(Et)(OtBu)]$_2$, SiH$_2$[CH$_2$—SiH(Et)(OiBu)]$_2$, SiH$_2$[CH$_2$—SiH(iPr)(OMe)]$_2$, SiH$_2$[CH$_2$—SiH(iPr)(OEt)]$_2$, SiH$_2$[CH$_2$—SiH(iPr)(OiPr)]$_2$, SiH$_2$[CH$_2$—SiH(iPr)(OnPr)]$_2$, SiH$_2$[CH$_2$—SiH(iPr)(OnBu)]$_2$, SiH$_2$[CH$_2$—SiH(iPr)(OtBu)]$_2$, SiH$_2$[CH$_2$—SiH(iPr)(OiBu)]$_2$, SiH$_2$[CH$_2$—SiH(nPr)(OMe)]$_2$, SiH$_2$[CH$_2$—SiH(nPr)(OEt)]$_2$, SiH$_2$[CH$_2$—SiH(nPr)(OnPr)]$_2$, SiH$_2$[CH$_2$—SiH(nPr)(OiPr)]$_2$, SiH$_2$[CH$_2$—SiH(nPr)(OnBu)]$_2$, SiH$_2$[CH$_2$—SiH(nPr)(OtBu)]$_2$, SiH$_2$[CH$_2$—SiH(nPr)(OiBu)]$_2$, SiH$_2$[CH$_2$—SiH(nBu)(OMe)]$_2$, SiH$_2$[CH$_2$—SiH(nBu)(OEt)]$_2$, SiH$_2$[CH$_2$—SiH(nBu)(OnPr)]$_2$, SiH$_2$[CH$_2$—SiH(nBu)(OiPr)]$_2$, SiH$_2$[CH$_2$—SiH(nBu)(OnBu)]$_2$, SiH$_2$[CH$_2$—SiH(nBu)(OtBu)]$_2$, SiH$_2$[CH$_2$—SiH(nBu)(OiBu)]$_2$, SiH$_2$[CH$_2$—SiH(tBu)(OMe)]$_2$, SiH$_2$[CH$_2$—SiH(tBu)(OEt)]$_2$, SiH$_2$[CH$_2$—SiH(tBu)(OnPr)]$_2$, SiH$_2$[CH$_2$—SiH(tBu)(OiPr)]$_2$, SiH$_2$[CH$_2$—SiH(tBu)(OnBu)]$_2$, SiH$_2$[CH$_2$—SiH(tBu)(OtBu)]$_2$, SiH$_2$[CH$_2$—SiH(tBu)(OiBu)]$_2$, SiH$_2$[CH$_2$—SiH(iBu)(OMe)]$_2$, SiH$_2$[CH$_2$—SiH(iBu)(OEt)]$_2$, SiH$_2$[CH$_2$—SiH(iBu)(OnPr)]$_2$, SiH$_2$[CH$_2$—SiH(iBu)(OiPr)]$_2$, SiH$_2$[CH$_2$—SiH(iBu)(OnBu)]$_2$, SiH$_2$[CH$_2$—SiH(iBu)(OtBu)]$_2$, SiH$_2$[CH$_2$—SiH(iBu)(OiBu)]$_2$, SiH$_2$[CH$_2$—SiH(SiMe$_3$)(OMe)]$_2$, SiH$_2$[CH$_2$—SiH(SiMe$_3$)(OEt)]$_2$, SiH$_2$[CH$_2$—SiH(SiMe$_3$)(OnPr)]$_2$, SiH$_2$[CH$_2$—SiH(SiMe$_3$)(OiPr)]$_2$, SiH$_2$[CH$_2$—SiH(SiMe$_3$)(OnBu)]$_2$, SiH$_2$[CH$_2$—SiH(SiMe$_3$)(OtBu)]$_2$, and SiH$_2$[CH$_2$—SiH(SiMe$_3$)(OiBu)]$_2$.

Exemplary compounds wherein b=0, c=2, x=1, y=0, and z=2 include SiH$_2$[CH$_2$—Si(Me)$_2$(OMe)]$_2$, SiH$_2$[CH$_2$—Si(Me)$_2$(OEt)]$_2$, SiH$_2$[CH$_2$—Si(Me)$_2$(OiPr)]$_2$, SiH$_2$[CH$_2$—Si(Me)$_2$(OnPr)]$_2$, SiH$_2$[CH$_2$—Si(Me)$_2$(OnBu)]$_2$, SiH$_2$[CH$_2$—Si(Me)$_2$(OiBu)]$_2$, SiH$_2$[CH$_2$—Si(Me)$_2$(OtBu)]$_2$, SiH$_2$[CH$_2$—Si(Et)$_2$(OMe)]$_2$, SiH$_2$[CH$_2$—Si(Et)$_2$(OEt)]$_2$, SiH$_2$[CH$_2$—Si(Et)$_2$(OiPr)]$_2$, SiH$_2$[CH$_2$—Si(Et)$_2$(OnPr)]$_2$, SiH$_2$[CH$_2$—Si(Et)$_2$(OnBu)]$_2$, SiH$_2$[CH$_2$—Si(Et)$_2$(OtBu)]$_2$, SiH$_2$[CH$_2$—Si(Et)$_2$(OiBu)]$_2$, SiH$_2$[CH$_2$—Si(iPr)$_2$(OMe)]$_2$, SiH$_2$[CH$_2$—Si(iPr)$_2$(OEt)]$_2$, SiH$_2$[CH$_2$—Si(iPr)$_2$(OiPr)]$_2$, SiH$_2$[CH$_2$—Si(iPr)$_2$(OnPr)]$_2$, SiH$_2$[CH$_2$—Si(iPr)$_2$(OnBu)]$_2$, SiH$_2$[CH$_2$—Si(iPr)$_2$(OtBu)]$_2$, SiH$_2$[CH$_2$—Si(iPr)$_2$(OiBu)]$_2$, SiH$_2$[CH$_2$—Si(nPr)$_2$(OMe)]$_2$, SiH$_2$[CH$_2$—Si(nPr)$_2$(OEt)]$_2$, SiH$_2$[CH$_2$—Si(nPr)$_2$(OnPr)]$_2$, SiH$_2$[CH$_2$—Si(nPr)$_2$(OiPr)]$_2$, SiH$_2$[CH$_2$—Si(nPr)$_2$(OnBu)]$_2$, SiH$_2$[CH$_2$—Si(nPr)$_2$(OtBu)]$_2$, SiH$_2$[CH$_2$—Si(nPr)$_2$(OiBu)]$_2$, SiH$_2$[CH$_2$—Si(nBu)$_2$(OMe)]$_2$, SiH$_2$[CH$_2$—Si(nBu)$_2$(OEt)]$_2$, SiH$_2$[CH$_2$—Si(nBu)$_2$(OnPr)]$_2$, SiH$_2$[CH$_2$—Si(nBu)$_2$(OiPr)]$_2$, SiH$_2$[CH$_2$—Si(nBu)$_2$(OnBu)]$_2$, SiH$_2$[CH$_2$—Si(nBu)$_2$ (OtBu)]$_2$, SiH$_2$[CH$_2$—Si(nBu)$_2$(OiBu)]$_2$, SiH$_2$[CH$_2$—Si(tBu)$_2$(OMe)]$_2$, SiH$_2$[CH$_2$—Si(tBu)$_2$(OEt)]$_2$, SiH$_2$[CH$_2$—Si(tBu)$_2$(OnPr)]$_2$, SiH$_2$[CH$_2$—Si(tBu)$_2$(OiPr)]$_2$, SiH$_2$[CH$_2$—Si(tBu)$_2$(OnBu)]$_2$, SiH$_2$[CH$_2$—Si(tBu)$_2$(OtBu)]$_2$, SiH$_2$[CH$_2$—Si(tBu)$_2$(OiBu)]$_2$, SiH$_2$[CH$_2$—Si(iBu)$_2$(OMe)]$_2$, SiH$_2$[CH$_2$—Si(iBu)$_2$(OEt)]$_2$, SiH$_2$[CH$_2$—Si(iBu)$_2$(OnPr)]$_2$, SiH$_2$[CH$_2$—Si(iBu)$_2$(OiPr)]$_2$, SiH$_2$[CH$_2$—Si(iBu)$_2$(OnBu)]$_2$, SiH$_2$[CH$_2$—Si(iBu)$_2$(OtBu)]$_2$, SiH$_2$[CH$_2$—Si(iBu)$_2$(OiBu)]$_2$, SiH$_2$[CH$_2$—Si(SiMe$_3$)$_2$(OMe)]$_2$, SiH$_2$[CH$_2$—Si(SiMe$_3$)$_2$(OEt)]$_2$, SiH$_2$[CH$_2$—Si(SiMe$_3$)$_2$(OnPr)]$_2$, SiH$_2$[CH$_2$—Si(SiMe$_3$)$_2$(OiPr)]$_2$, SiH$_2$-[CH$_2$—Si(SiMe$_3$)$_2$(OnBu)]$_2$, SiH$_2$[CH$_2$—Si(SiMe$_3$)$_2$(OtBu)]$_2$, and SiH$_2$[CH$_2$—Si(SiMe$_3$)$_2$(OiBu)]$_2$.

Exemplary compounds wherein b=0, c=2, x=2, y=0, and z=1 include
SiH$_2$[CH$_2$—Si(Me)(OMe)$_2$]$_2$, SiH$_2$[CH$_2$—Si(Me)(OEt)$_2$]$_2$, SiH$_2$[CH$_2$—Si(Me)(OiPr)$_2$]$_2$, SiH$_2$[CH$_2$—Si(Me)(OnPr)$_2$]$_2$, SiH$_2$[CH$_2$—Si(Me)(OnBu)$_2$]$_2$, SiH$_2$[CH$_2$—Si(Me)(OiBu)$_2$]$_2$, SiH$_2$[CH$_2$—Si(Me)(OtBu)$_2$]$_2$, SiH$_2$[CH$_2$—Si(Et)(OMe)$_2$]$_2$, SiH$_2$[CH$_2$—Si(Et)(OEt)$_2$]$_2$, SiH$_2$[CH$_2$—Si(Et)(OiPr)$_2$]$_2$, SiH$_2$[CH$_2$—Si(Et)(OnPr)$_2$]$_2$, SiH$_2$[CH$_2$—Si(Et)(OnBu)$_2$]$_2$, SiH$_2$[CH$_2$—Si(Et)(OtBu)$_2$]$_2$, SiH$_2$[CH$_2$—Si(Et)(OiBu)$_2$]$_2$, SiH$_2$[CH$_2$—Si(iPr)(OMe)$_2$]$_2$, SiH$_2$[CH$_2$—Si(iPr)(OEt)$_2$]$_2$, SiH$_2$[CH$_2$—Si(iPr)(OiPr)$_2$]$_2$, SiH$_2$[CH$_2$—Si(iPr)(OnPr)$_2$]$_2$, SiH$_2$[CH$_2$—Si(iPr)(OnBu)$_2$]$_2$, SiH$_2$[CH$_2$—Si(iPr)(OtBu)$_2$]$_2$, SiH$_2$[CH$_2$—Si(iPr)(OiBu)$_2$]$_2$, SiH$_2$[CH$_2$—Si(nPr)(OMe)$_2$]$_2$, SiH$_2$[CH$_2$—Si(nPr)(OEt)$_2$]$_2$, SiH$_2$[CH$_2$—Si(nPr)(OnPr)$_2$]$_2$, SiH$_2$[CH$_2$—Si(nPr)(OiPr)$_2$]$_2$, SiH$_2$[CH$_2$—Si(nPr)(OnBu)$_2$]$_2$, SiH$_2$[CH$_2$—Si(nPr)(OtBu)$_2$]$_2$, SiH$_2$[CH$_2$—Si(nPr)(OiBu)$_2$]$_2$, SiH$_2$[CH$_2$—Si(nBu)(OMe)$_2$]$_2$, SiH$_2$[CH$_2$—Si(nBu)(OEt)$_2$]$_2$, SiH$_2$[CH$_2$—Si(nBu)(OnPr)$_2$]$_2$, SiH$_2$[CH$_2$—Si(nBu)(OiPr)$_2$]$_2$, SiH$_2$[CH$_2$—Si(nBu)(OnBu)$_2$]$_2$, SiH$_2$[CH$_2$—Si(nBu)(OtBu)$_2$]$_2$, SiH$_2$[CH$_2$—Si(nBu)(OiBu)$_2$]$_2$, SiH$_2$[CH$_2$—Si(tBu)(OMe)$_2$]$_2$, SiH$_2$[CH$_2$—Si(tBu)(OEt)$_2$]$_2$, SiH$_2$[CH$_2$—Si(tBu)(OnPr)$_2$]$_2$, SiH$_2$[CH$_2$—Si(tBu)(OiPr)$_2$]$_2$, SiH$_2$[CH$_2$—Si(tBu)(OnBu)$_2$]$_2$, SiH$_2$[CH$_2$—Si(tBu)(OtBu)$_2$]$_2$, SiH$_2$[CH$_2$—Si(tBu)(OiBu)$_2$]$_2$, SiH$_2$[CH$_2$—Si(iBu)(OMe)$_2$]$_2$, SiH$_2$[CH$_2$—Si(iBu)(OEt)$_2$]$_2$, SiH$_2$[CH$_2$—Si(iBu)(OnPr)$_2$]$_2$, SiH$_2$[CH$_2$—Si(iBu)(OiPr)$_2$]$_2$, SiH$_2$[CH$_2$—Si(iBu)(OnBu)$_2$]$_2$, SiH$_2$[CH$_2$—Si(iBu)(OtBu)$_2$]$_2$, SiH$_2$[CH$_2$—Si(iBu)(OiBu)$_2$]$_2$, SiH$_2$[CH$_2$—Si(SiMe$_3$)(OMe)$_2$]$_2$, SiH$_2$[CH$_2$—Si(SiMe$_3$)(OEt)$_2$]$_2$, SiH$_2$[CH$_2$—Si(SiMe$_3$)(OnPr)$_2$]$_2$, SiH$_2$[CH$_2$—Si(SiMe$_3$)(OiPr)$_2$]$_2$, SiH$_2$[CH$_2$—Si(SiMe$_3$)(OnBu)$_2$]$_2$, SiH$_2$[CH$_2$—Si(SiMe$_3$)(OtBu)$_2$]$_2$, and SiH$_2$[CH$_2$—Si(SiMe$_3$)(OiBu)$_2$]$_2$.

The disclosed compounds are synthesized by reacting a Grignard reagent having the formula Si(OR')$_x$H$_y$R$_z$(CH$_2$MgX) with a quenching agent having the formula SiCl$_a$(OR)$_b$(H)$_c$, wherein a=1 to 3; b=0 to 3; c=0 to 2; a+b+c=4; x=0 to 3; y=0 to 1; z=0 to 3; x+y+z=3; X=Cl, Br, or I ("halide" atoms); each R is independently a C1 to C5 linear or branched alkyl group or a trimethylsilyl group; and each R' is independently a C1 to C5 linear or branched alkyl group.

The Grignard reagent and the quenching agent are reacted in a polar solvent, such as tetrahydrofuran, diethyl ether, or dimethoxyethane. The molar ratio of Grignard reagent to quenching agent is between approximately 0.8 to approximately 4.5. The number of halide atoms in the quenching agent further determines the molar ratio of Grignard reagent to quenching agent. For example, if the quenching agent contains one halide atom, the molar ratio of Grignard reagent to quenching agent should range from 0.8 to 1.5. If the quenching agent contains two halide atoms, the molar ratio of Grignard reagent to quenching agent should range from 1.6 to 3. If the quenching agent contains three halide atoms, the molar ratio of Grignard reagent to quenching agent should range from 2.4 to 4.5.

The quenching agent "deactivates" the Grignard reagent by reacting with the Grignard reagent to produce the disclosed compound and a Mg salt compound. This quenching action prevents the Grignard reagent from reacting with itself and producing undesired products, such as trisilacyclohexane compounds. The number of halide molecules in the quenching agent further determines the number of silicon molecules in the disclosed compound (not including the Si atom in any pendant trimethylsilyl groups). For example, if the quenching agent contains one halide atom, the disclosed compound will contain two silicon atoms. If the quenching agent contains two halide atoms, the disclosed compound will contain three silicon atoms. If the quenching agent contains three halide atoms, the disclosed compound will contain four silicon atoms.

In situ quenching occurs when the Grignard reagent, as it forms, immediately reacts with the quenching agent. As will be described in more detail infra, the quenching agent and the Si(OR')$_x$H$_y$R$_z$(CH$_2$X) reactant used to form the Grignard reagent may be mixed prior to reaction with magnesium, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group. Alternatively, the quenching agent may be added to the Grignard reagent/magnesium mixture after the Grignard commences and the temperature of the mixture has been reduced to between approximately 0° C. and approximately 20° C.

Preferably, the Grignard reagent and quenching agent are mixed in an anhydrous polar solvent, resulting in improved yield. One of ordinary skill in the art will recognize how to produce the anhydrous polar solvent. For example, the polar solvent, benzophenone, and sodium may be mixed and refluxed, followed by distillation (referred to as Na treated). Alternatively, the polar solvent may be filtered through activated alumina and then degassed by N$_2$ bubbling.

The Grignard reagent and the quenching agent may be mixed with the polar solvent at temperatures ranging from approximately 0° C. to approximately 70° C., preferably from approximately 0° C. to approximately 50° C. In lab scale testing, the mixture was initially heated to 30° C. to help begin the reaction. One of ordinary skill in the art will recognize that the reaction is exothermic and therefore that the temperature of the reaction may increase as the reaction progresses. Preferably, the temperature does not exceed 70° C., and more preferably it remains less than 50° C. Optimal results were obtained by cooling the mixture to a temperature between approximately 0° C. and approximately 20° C. after the exothermic reaction commences. The mixing may occur for a duration of approximately 1 hour to approximately 48 hours, preferably for approximately 8 hours. One of ordinary skill in the art will recognize that the duration of the reaction will depend upon the temperature and the number of chlorine atoms in the quenching agent, with more chlorine atoms requiring a longer reaction time. One of ordinary skill in the art will further recognize that these reactions must be performed in an inert, anhydrous atmosphere, preferably under a nitrogen atmosphere.

After mixing, the polar solvent may be removed by distillation. The remaining material is mixed with a nonpolar solvent, such as pentane, hexane, or heptane, and subsequently filtered to produce the desired compound.

Applicants believe that the alkoxy group of the quenching agents causes the Grignard reagents to preferentially react with the at least one Si—Cl bond of the quenching agents. In other words, the alkoxy group acts as a protecting group to the Si atom during the reaction of the Grignard reagent with the quenching agent. Similarly, Applicants have surprisingly discovered that the hydride ligand of the quenching agents remains inert during the reaction of Grignard reagent and the quenching agent, once again causing the Grignard reagent to preferentially react with the at least one Si—Cl bond of the quenching agent. The use of the hydrogen or alkoxy group provides the ability of the disclosed synthesis methods to selectively generate the target compound in high yield. In contrast, as illustrated in the following comparative example, use of $SiCl_4$ as the quenching agent yields the undesirable mixture of $SiCl_{4-x}(CH_2—Si(OEt)_3)_x$ (x=1, 2, 3).

In some embodiments, a=2, b=2, and c=0 produce quenching agents having the formula $SiCl_2(OR)_2$, wherein each R is independently a C1 to C5 linear or branched alkyl group or a trimethylsilyl group. Exemplary quenching agents include $SiCl_2(OMe)_2$, $SiCl_2(OEt)_2$, $SiCl_2(OiPr)_2$, $SiCl_2(OnPr)_2$, $SiCl_2(OnBu)_2$, $SiCl_2(OtBu)_2$, $SiCl_2(OsBu)_2$, $SiCl_2(OPentane)_2$, or $SiCl_2(OSiMe_3)_2$. These quenching agents are not commercially available, but may be synthesized by methods known in the art.

In some embodiments, b=0 to produce quenching agents having the formula $SiCl_a(H)_{4-a}$, wherein a=1 to 3. Exemplary quenching agents include $SiClH_3$, $SiH_2Cl_2$, or $SiHCl_3$. These quenching agents are commercially available.

In some embodiments, c=2 to produce quenching agents having the formula $SiCl_a(OR)_{2-a}H_2$, wherein a=1-2 and each R is independently a C1 to C5 linear or branched alkyl group or a trimethylsilyl group. Exemplary quenching agents include $SiH_2Cl_2$, $SiH_2Cl(OMe)$, $SiH_2Cl(OEt)$, $SiH_2Cl(OiPr)$, $SiH_2Cl(OnPr)$, $SiH_2Cl(OnBu)$, $SiH_2Cl(OtBu)$, $SiH_2Cl(OsBu)$, $SiH_2Cl(O\text{-Pentane})$, or $SiH_2Cl(OSiMe_3)$. These quenching agents are commercially available.

In some embodiments, b=0 and c=2 to produce the quenching agent $SiC_{12}H_2$. This quenching agent is commercially available.

In some embodiments, x=3, y=0, z=0, and R'=Me or Et to produce Grignard reagents having the formula $S1(OMe)_3(CH_2MgX)$ or $Si(OEt)_3(CH_2MgX)$, wherein X=Cl, Br, or I. Exemplary reagents include $Si(OMe)_3(CH_2MgCl)$, $Si(OEt)_3(CH_2MgCl)$, $Si(OMe)_3(CH_2MgBr)$, $Si(OEt)_3(CH_2MgBr)$, $Si(OMe)_3(CH_2MgI)$, and $Si(OEt)_3(CH_2MgI)$.

In some embodiments, y=1 to produce Grignard reagents having the formula $SiH(OR')_x(R)_{2-x}(CH_2MgX)$, wherein x=0 to 2; X=Cl, Br, or I; each R is independently a C1 to C5 linear or branched alkyl group or a trimethylsilyl group; and each R' is independently a C1 to C5 linear or branched alkyl group. Exemplary reagents include $SiH(OMe)_2(CH_2MgCl)$, $SiH(OMe)_2(CH_2MgBr)$, $SiH(OMe)_2(CH_2MgI)$, $SiH(OEt)_2(CH_2MgCl)$, $SiH(OEt)_2(CH_2MgBr)$, $SiH(OEt)_2(CH_2MgI)$, $SiH(OiPr)_2(CH_2MgCl)$, $SiH(OiPr)_2(CH_2MgBr)$, $SiH(OiPr)_2(CH_2MgI)$, $SiH(OnPr)_2(CH_2MgCl)$, $SiH(OnPr)_2(CH_2MgBr)$, $SiH(OnPr)_2(CH_2MgI)$, $SiH(OnBu)_2(CH_2MgCl)$, $SiH(OnBu)_2(CH_2MgBr)$, $SiH(OnBu)_2(CH_2MgI)$, $SiH(OtBu)_2(CH_2MgCl)$, $SiH(OtBu)_2(CH_2MgBr)$, $SiH(OtBu)_2(CH_2MgI)$, $SiH(OMe)(Me)(CH_2MgCl)$, $SiH(OMe)(Me)(CH_2MgBr)$, $SiH(OMe)(Me)(CH_2MgI)$, $SiH(OEt)(Et)(CH_2MgCl)$, $SiH(OEt)(Et)(CH_2MgBr)$, $SiH(OEt)(Et)(CH_2MgI)$, $SiH(OiPr)(iPr)(CH_2MgCl)$, $SiH(OiPr)(iPr)(CH_2MgBr)$, $SiH(OiPr)(iPr)(CH_2MgI)$, $SiH(OnPr)(nPr)(CH_2MgCl)$, $SiH(OnPr)(nPr)(CH_2MgBr)$, $SiH(OnPr)(nPr)(CH_2MgI)$, $SiH(OnBu)(nBu)(CH_2MgCl)$, $SiH(OnBu)(nBu)(CH_2MgBr)$, $SiH(OnBu)(nBu)(CH_2MgI)$, $SiH(OtBu)(tBu)(CH_2MgCl)$, $SiH(OtBu)(tBu)(CH_2MgBr)$, $SiH(OtBu)(tBu)(CH_2MgI)$, $SiH(OMe)(SiMe_3)(CH_2MgCl)$, $SiH(OMe)(SiMe_3)(CH_2MgBr)$, $SiH(OMe)(SiMe_3)(CH_2MgI)$, $SiHMe_2(CH_2MgCl)$, $SiHMe_2(CH_2MgBr)$, $SiHMe_2(CH_2MgI)$, $SiHEt_2(CH_2MgCl)$, $SiHEt_2(CH_2MgBr)$, $SiHEt_2(CH_2MgI)$, $SiH(iPr)_2(CH_2MgCl)$, $SiH(iPr)_2(CH_2MgBr)$, $SiH(iPr)_2(CH_2MgI)$, $SiH(nPr)_2(CH_2MgCl)$, $SiH(nPr)_2(CH_2MgBr)$, $SiH(nPr)_2(CH_2MgI)$, $SiH(nBu)_2(CH_2MgCl)$, $SiH(nBu)_2(CH_2MgBr)$, $SiH(nBu)_2(CH_2MgI)$, $SiH(tBu)_2(CH_2MgCl)$, $SiH(tBu)_2(CH_2MgBr)$, $SiH(tBu)_2(CH_2MgI)$, $SiH(SiMe_3)_2(CH_2MgCl)$, $SiH(SiMe_3)_2(CH_2MgBr)$, or $SiH(SiMe_3)_2(CH_2MgI)$.

In some embodiments, z=0 to produce Grignard reagents having the formula $Si(OR')_xH_y(CH_2MgX)$, wherein x=0 to 3; y=0 to 1; x+y=3; X=Cl, Br, or I; and each R' is independently a C1 to C5 linear or branched alkyl group. Exemplary reagents include $Si(OMe)_3(CH_2MgCl)$, $Si(OEt)_3(CH_2MgCl)$, $Si(OMe)_3(CH_2MgBr)$, $Si(OEt)_3(CH_2MgBr)$, $Si(OMe)_3(CH_2MgI)$, $Si(OEt)_3(CH_2MgI)$, $Si(OiPr)_3(CH_2MgCl)$, $Si(OiPr)_3(CH_2MgBr)$, $Si(OiPr)_3(CH_2MgI)$, $Si(OnPr)_3(CH_2MgCl)$, $Si(OnPr)_3(CH_2MgBr)$, $Si(OnPr)_3(CH_2MgI)$, $SiH(OMe)_2(CH_2MgCl)$, $SiH(OMe)_2(CH_2MgBr)$, $SiH(OMe)_2(CH_2MgI)$, $SiH(OEt)_2(CH_2MgCl)$, $SiH(OEt)_2(CH_2MgBr)$, $SiH(OEt)_2(CH_2MgI)$, $SiH(OiPr)_2(CH_2MgCl)$, $SiH(OiPr)_2(CH_2MgBr)$, $SiH(OiPr)_2(CH_2MgI)$, $SiH(OnPr)_2(CH_2MgCl)$, $SiH(OnPr)_2(CH_2MgBr)$, $SiH(OnPr)_2(CH_2MgI)$, $SiH(OnBu)_2(CH_2MgCl)$, $SiH(OnBu)_2(CH_2MgBr)$, $SiH(OnBu)_2(CH_2MgI)$, $SiH(OtBu)_2(CH_2MgCl)$, $SiH(OtBu)_2(CH_2MgBr)$, or $SiH(OtBu)_2(CH_2MgI)$.

The Grignard reagents may be synthesized by reacting $Si(OR')_xH_yR_z(CH_2X)$ over magnesium, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group. The $Si(OR')_xH_yR_z(CH_2X)$ reactants are commercially available.

The synthesis of the Grignard reagent may occur in the same vessel as that in which the Grignard reagent and the quenching agent are reacted. The $Si(OR')_xH_yR_z(CH_2X)$ reacta\nt and quenching agent may be mixed together before reaction with magnesium. Alternatively, the $Si(OR')_xH_yR_z(CH_2X)$ reactant may be added to Mg, followed by addition of the quenching agent. One of ordinary skill in the art will recognize that addition of an activator, such as 1,2-dibromoethane ($BrCH_2CH_2Br$), iodide ($I_2$), or pure HCl, may be needed to activate the Mg surface. The activator may be added to the Grignard reagent before addition of the $Si(OR')_xH_yR_z(CH_2X)$ reactant and/or quenching agent.

The OR' alkoxy group of the $Si(OR')_xH_yR_z(CH_2X)$ reactant is more reactive than the R alkyl group. As a result, upon exposure to Mg, the $Si(OR')_xH_yR_z(CH_2X)$ reactant may react upon itself to form the cyclic molecule ($—CH_2—Si(OR')_xH_yR_z—)_3$. Therefore, when the reactant contains at least one alkoxy group, the synthesis of the Grignard reagent preferably occurs in the same vessel as that in which the reaction between the Grignard reagent and the quenching agent occurs. In this embodiment, the $Si(OR')_xH_yR_z(CH_2X)$ reactant, Mg, and the quenching agent are added to a flask containing the polar solvent and mixed (i.e., in situ quenching). The Mg may be activated by an activator prior to adding the $Si(OR')_xH_yR_z(CH_2X)$ reactant and the quenching agent. The quenching agent prevents the Grignard reagent formed by the reaction of the $Si(OR')_xH_yR_z(CH_2X)$ reactant and the Mg from reacting with itself and producing undesired products, such as trisilacyclohexane compounds. The quenching agent "deactivates" the Grignard reagent by reacting with the Grignard reagent to produce the disclosed compound and a Mg salt compound. As discussed previously, the mixing may occur at temperatures ranging from approximately 0° C. to approximately 70° C., preferably from approximately 0° C. to approximately 50° C. One of ordinary skill in the art will recognize that the reaction is exothermic and therefore that the temperature of the reaction may increase as the reaction progresses. As discussed previously, the temperature of the reaction mixture may initially range from approximately 20° C. to approximately 70° C. and may then be cooled to approximately 0° C. to approximately 20° C. after confirming that the exothermic reaction has started. The mixing is completed when no Mg remains.

After mixing, the polar solvent may be removed by distillation. The remaining material is mixed with a nonpolar solvent, such as pentane, butane, or hexane, and subsequently filtered to produce the desired compound.

The synthesized compounds may be reduced to form a compound having the formula $SiH_{b+c}[CH_2—SiH_{x+y}R_z]_{4-b-c}$, wherein b=0 to 3; c=0 to 2; b+c=1 to 3; x=0 to 3; y=0 to 1; z=0 to 3; x+y+z=3; and each R is independently a C1 to C5 linear or branched alkyl group or a trimethylsilyl group. $AlLiH_4$ in ether may be used as the reducing agent. The molar ratio of $AlLiH_4$ to $Si(OR)_b(H)_c[CH_2—Si(OR')_xH_yR_z]_a$ is between approximately (b+ax)/4 and approximately (b+ax)/2, wherein b=0 to 3, a=1 to 3, and x=0 to 3. Preferably, the molar ratio of $AlLiH4$ to $Si(OR)_b(H)_c[CH_2—Si(OR')_xH_yR_z]_a$ is approximately 1.2[(b+ax)/4] to approximately 1.5[(b+ax)/4]. $NaBH_4$ in ether may alternately be used as the reducing agent. The molar ratio of $NaBH_4$ to $Si(OR)_b(H)_c[CH_2—Si(OR')_xH_yR_z]_a$ is between (b+ax)/4 and approximately (b+ax)/2, wherein b=0 to 3, a=1 to 3, and x=0 to 3. Preferably, the molar ratio of $AlLiH4$ to $Si(OR)_b(H)_c[CH_2—Si(OR')_xH_yR_z]_a$ is approximately 1.2[(b+ax)/4] to approximately 1.5[(b+ax)/4]. During reduction, the at least one alkoxy group of the quenching agent that had formerly acted as a protecting group is reactive to the reducing agent and easily reduced to H.

In one preferred embodiment, $SiH[CH_2—Si(OEt)_3]_3$ is synthesized by reacting a Grignard reagent having the formula $Si(OEt)_3(CH_2MgCl)$ with a compound having the formula $SiHCl_3$. The $Si(OEt)_3(CH_2MgCl)$ Grignard reagent is formed in situ by reacting $Si(OEt)_3(CH_2Cl)$ over magnesium. Addition of an activator may be necessary to activate the Mg surface. The $Si(OEt)_3(CH_2MgCl)$ Grignard reagent may be formed in the same vessel as that in which the Grignard reagent and the quenching agent are reacted. Preferably, the $Si(OEt)_3(CH_2MgCl)$ Grignard reagent is formed in the same vessel as that in which the Grignard reagent and the quenching agent are reacted.

This embodiment is preferred because the $SiHCl_3$ reactant is commercially available and (currently) inexpensive. Use of the $SiHCl_3$ reduces the potential for forming unwanted multi-substituted products. Finally, the $SiHCl_3$ is a liquid, making it easy to handle.

$SiH[CH_2—Si(OEt)_3]_3$ may be reduced to form a compound having the formula $SiH[CH_2—SiH_3]_3$. $AlLiH_4$ in ether may be used as the reducing agent. The molar ratio of $AlLiH_4$ to $SiH[CH_2—Si(OEt)_3]_3$ is approximately 2. Alternatively, $NaBH_4$ in ether may be the reducing agent. The molar ratio of $NaBH_4$ to $SiH[CH_2—Si(OEt)_3]_3$ is approximately 2.

EXAMPLES

The following examples illustrate experiments performed in conjunction with the disclosure herein. The examples are not intended to be all inclusive and are not intended to limit the scope of disclosure described herein.

Comparative Example 2 molar equivalents $ClCH_2Si(OEt)_3$, 2 molar equivalents of Mg (sanded ribbon) and 1 molar equivalent of $SiCl_4$ were mixed with tetrahydrofuran (THF) (Na treated) in flask. The mixture was stirred until Mg disappeared and THF was removed by distillation. Pentane was added to extract a mixture including the $(EtO)_3SiCH_2Si(Cl)_2CH_2Si(OEt)_3$ product. After removal of pentane, 71% crude yield was obtained, including impurities, formed by the reaction of 3 $ClMgCH_2—Si(OEt)_3$ molecules with $SiCl_4$, yielding $SiCl(CH_2—Si(OEt)_3)_3$.

Upon reduction by $AlLiH_4$ in ether, the obtained reduced mixture (all Cl or OEt being substituted by H to form the target compound $H_3SiCH_2SiH_2CH_2SiH_3$) is analyzed by gas chromatography shown in FIG. 1, showing a large concentration of branched carbosilane $SiH(CH_2—SiH_3)_3$ and partially reacted product $(CH_2(SiH_3)_2)$.

Example 1

Synthesis of $HSi[CH_2SiH_3]_3$

Jul. 19, 2012

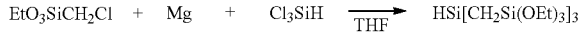

CMTES (chloromethyltriethoxysilane) was slowly added to Mg suspension. No increase in temperature observed. Heated with heat gun to 30° C. At this point saw temperature to continue to rise on own and solution started turing brown. Quickly cooled with an ice bath. Solution dropped in temperature to approximately 13° C. Allowed to stir approximately 1 hour. Once temperature dropped to approximately 5° C., TCS (trichlorosilane) slowly added. Stopped adding when there was approximately 1 mL still left to add. Removed ice bath and allowed to stir approximately 30 minutes before adding final TCS. Solids had begun to form. GCMS (gas chromatography/mass spectrometry) showed what appears to be the desired product as main species but also some disubstituted and other small (lighter) impurities.

Jul. 20, 2012

Solution was stirred at room temperature overnight. Volatiles were removed under vacuum. The solids were washed with pentane and filtered through a pad of Celite.

Jul. 23, 2012

Volatiles were removed under vacuum. 16 g of a pale yellow liquid collected.

16 g/560=0.028 mol x 9=0.257 mol OEt 0.257 mol OEt (1 mol $LiAlH_4$/4 mol H⁻) (1 L/1 mol $LiAlH_4$)=64 mL To add 10% excess=70 mL $LiAlH_4$ Jul. 24, 2012

GCMS shows desired product at a retention time of approximatley 7 minutes (TSP approximately 8 minutes). Anhydrous dodecane was added to the suspension and volatiles were then vacuum transferred to another schlenk flask.

16g 70mL EXP 4.6g 0.023 mol 0.07 mol theo: % yield GCMS of volatiles shows very small trace of desired product (too dilute ? still in solids). GCMS of solids suspension did show desired product still present. Tried to vacuum transfer more volatiles from the solids. Unable to take GCMS of solids suspension afterwards because too visous to suck up with syringe.

Jul. 26, 2012

Did a quick vacuum distillation of solid suspension. Collected fraction at 30-40 milliTorr 47-49° C. When temperature began to creep higher and pressure lower, distillation was stopped. Also solids were beginning to burn due to poor stirring.
GCMS show desired product along with ether and dodecane. Final isolation not attempted at this time.

Example 2

Synthesis of HSi[CH$_2$SiH$_3$]$_3$

Figure 2:
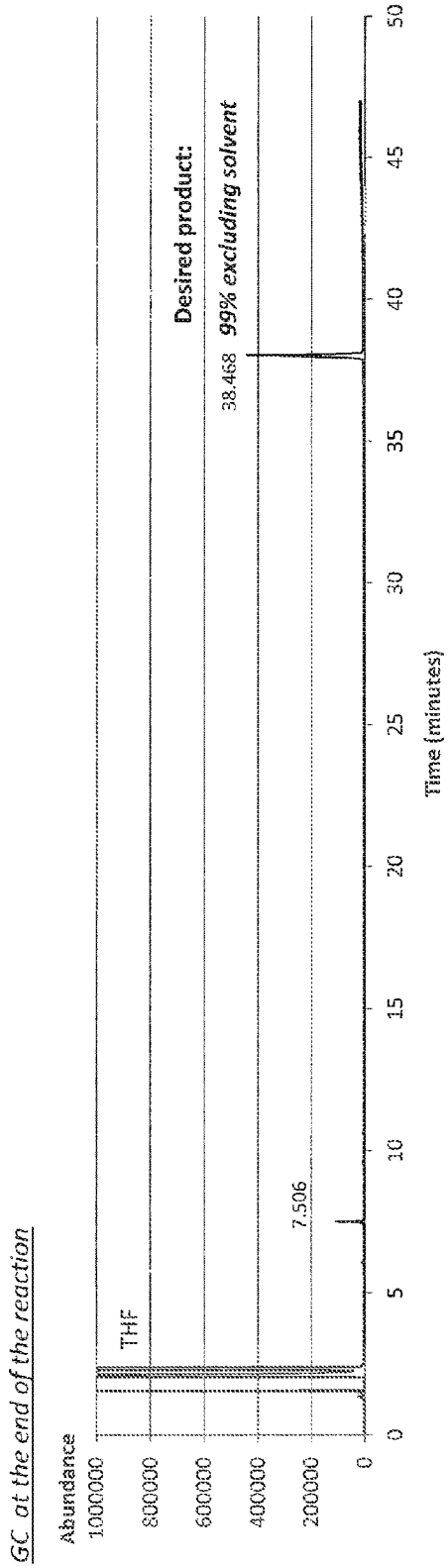
FIG. 2 is GCMS graph of $HSi[CH_2Si(OEt)_3]_3$ obtained in Example 2.
Figure 3:
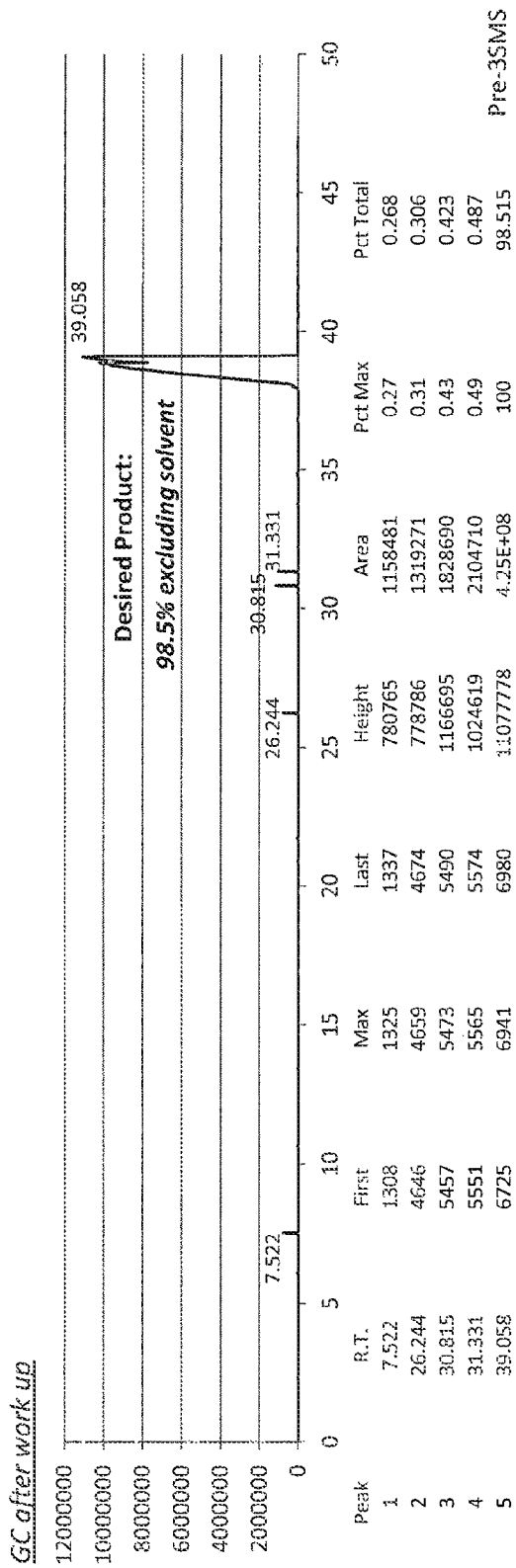
FIG. 3 is a GCMS graph of $HSi[CH_2Si(OEt)_3]_3$ of Example 2 after work up.

6 Aug. 2012
3 ClSi(OEt)$_3$+3 Mg+1 HSiCl$_3$→>HSi[CH$_2$Si(OEt)$_3$]$_3$ A B C D
100 g Starting material (A; 1.00 equiv; 470 mmol)
300 mL THF (3.00 vol Equiv)
11.4 g Mg (1.00 equiv; 470 mmol)
21.0 g Reactant 3 (C, 0.33 equiv; 155 mmol)
To a 1 L round bottom 3 neck flask with additional funnel and a thermometer, Mg was suspended in THF.
0.5 mL of Br$_2$C$_2$H$_4$ was added while stirring.
The starting material A (triethoxy(chloromethyl)silane) was dropwise with the dropping funnel within 2 hours. When temperature began to increase to 30° C., the reaction mixture was cooled to 0° C. and addition started again. Reaction mixture stirred for 2 hours with temperature between 0° C. to 10° C.
Addition of the HSiCl$_3$ at 10° C. Small exothermy temperature to 20° C.
Addition really slow and reaction mixture kept on ice bath. Once the addition is over, the mixture was stirred overnight.
Aug. 7, 2012
Reaction checked by GCMS=STSP-01/Manual injection TSA method)
THF removed by vacuum.
Pentane was added (500 mL) to precipitate the salts, washed at least 8 times with small amount of pentane (approximately 200 mL each)
Pentane was removed by vacuum. GCMS=STSP-02 Manual injection TSA Method
The GCMS results for the product obtained at the end of the reaction are provided in FIG. 2. The GCMS results for the product obtained after work up are provided in FIG. 3.
Weight obtained=80.7 g
Purity by GCMS=98.5% (via integration)
Yield 91% mol/mol
Aug. 9, 2012

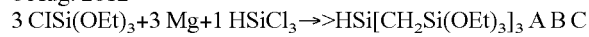

HSi[CH$_2$Si(OEt)$_3$]$_3$+LiAlH$_4$→>HSi[CH$_2$SiH$_3$]$_3$

A B Ether MW=164.50
M=23.70 g theoric weight
80.7 g Trisubstitute TSP (A; 1.00 equiv; 144 mmol)
200 mL diethyl ether (2.48 volEquiv)
12.3 g LiAlH$_4$ (B; 1 M in ether (ie 324 mL); 2.25 equiv; 324 mmol)

Figure 4:
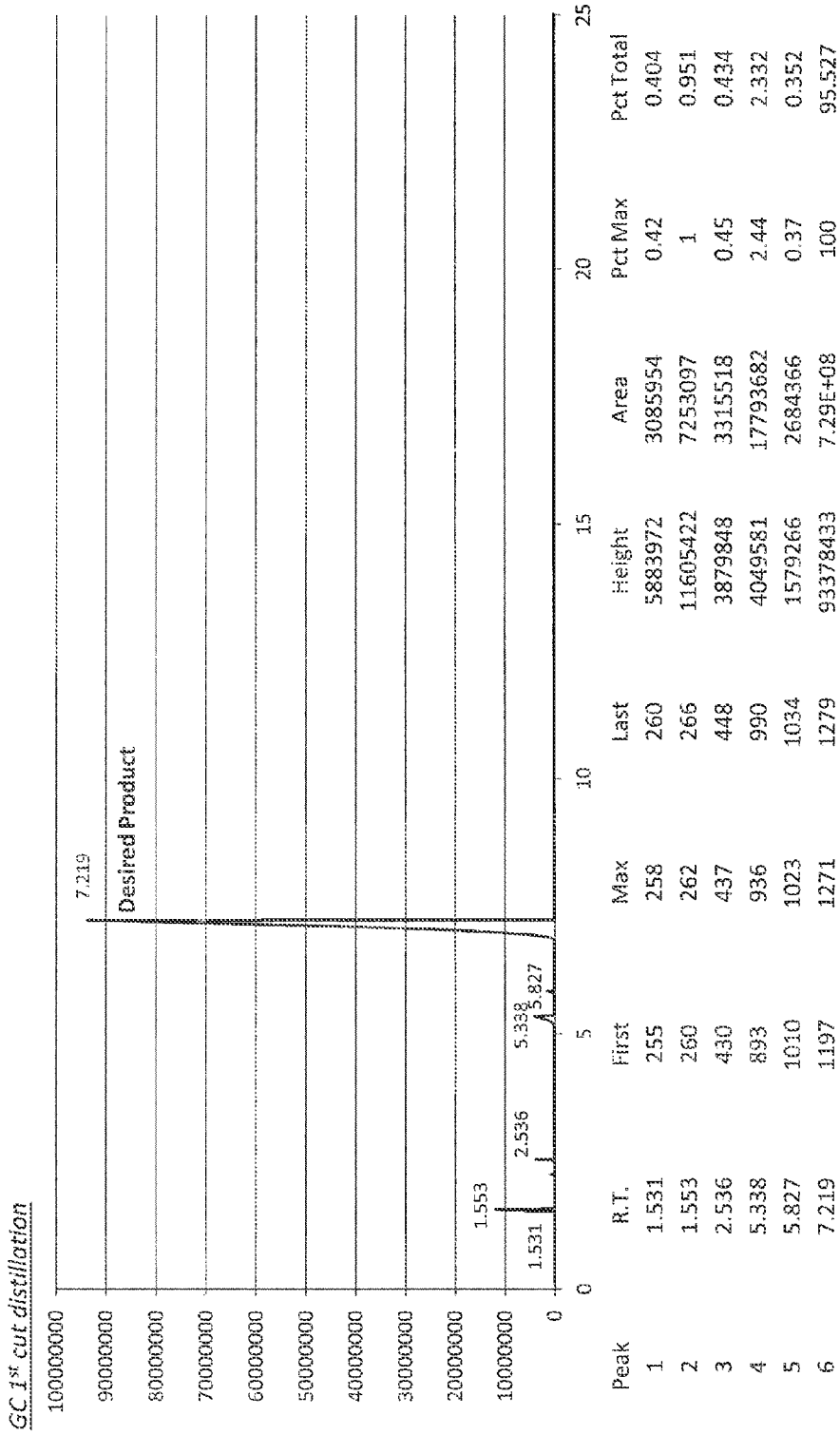
FIG. 4 is a GCMS graph of $HSi[CH_2SiH_3]_3$ obtained after first cut distillation in Example 2.
Figure 5:
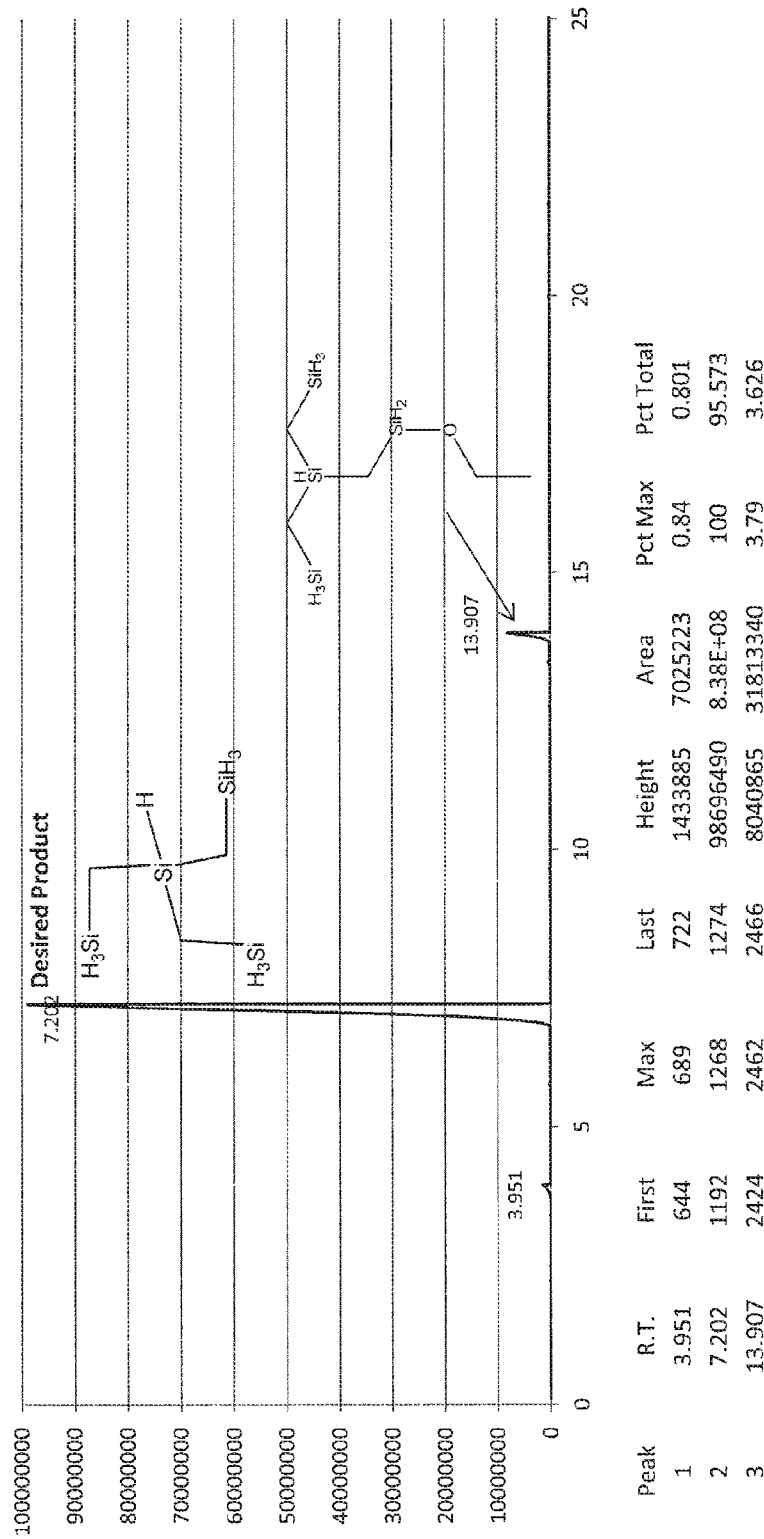
FIG. 5 is a GCMS graph of $HSi[CH_2SiH_3]_3$ obtained after second cut distillation in Example 2.

Scale up with 80.7 g starting material/23.7 g of desired product
In a 3 neck round bottom flask (1 L), the product obtained was suspended in 200 mL of ether in an atmosphere of Argon at RT (room temperature).
Then LiAlH$_4$ was added dropwise within 3 hours with temperature control on bath of dry ice.
Directly after the beginning of the addition, mixture became cloudy/white.
Once addition is over, the mixture was stirred overnight at RT.
Aug. 10, 2012
GCMS=STSP2-01
Ether removed by vacuum GCMS–STSP2-06
Aug. 13, 2012
Distillation was performed.
Under vacuum (120 mmTorr–50 mmTorr)/RT→4.9 g $1^{st}$ cut
Under vauum (120 mmTorr–50 mmTorr)/25° C. to 50° C.→12.7 g $2^{nd}$ cut
Left over=600 mg residue and celite
Total weight=16.8 g Yield=71% mol/mol
The GCMS for the first distillation is provided in FIG. 4 (GCMS–STSP2-09+NMR STSP2-09 (ok with predicted spectrum)).
The GCMS for the 2nd distillation is provided in FIG. 5 (GCMS–STSP2-10+NMR)
Additon of LiAlH$_4$ could have lead to better yield and complete reduction.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A method of synthesizing a carbosilane compound comprising reacting a Grignard reagent having the formula Si(OEt)$_3$(CH$_2$MgCl) with a quenching agent having the formula SiHCl$_3$ to produce SiH[CH$_2$—Si(OEt)$_3$]$_3$.

2. The method of claim 1, further comprising forming the Grignard reagent Si(OEt)$_3$(CH$_2$MgCl) by reacting Si(OEt)$_3$(CH$_2$Cl) over magnesium.

3. The method of claim 2, further comprising maintaining a temperature of formation of the Grignard reagent between about 0° C. to about 20° C.

4. The method of claim 3, wherein the step of forming the Grignard reagent Si(OEt)$_3$(CH$_2$MgCl) occurs in a same vessel as the step of reacting the Grignard reagent and the quenching agent.

5. The method of claim 4, further comprising reducing SiH[CH$_2$—Si(OEt)$_3$]$_3$ to form a compound having a formula SiH[CH$_2$—SiH$_3$]$_3$.

* * * * *

UNITED STATES PATENT AND TRADEMARK OFFICE
CERTIFICATE OF CORRECTION

| | | |
|---|---|---|
| PATENT NO. | : 8,859,797 B1 | Page 1 of 1 |
| APPLICATION NO. | : 13/973911 | |
| DATED | : October 14, 2014 | |
| INVENTOR(S) | : Zhiwen Wan et al. | |

It is certified that error appears in the above-identified patent and that said Letters Patent is hereby corrected as shown below:

On The Title Page, item (72) Inventors

Change "Ashulosh" to -- Ashutosh --.

Signed and Sealed this
Tenth Day of February, 2015

Michelle K. Lee
*Deputy Director of the United States Patent and Trademark Office*